(12) United States Patent
Lipowitz et al.

(10) Patent No.: US 10,330,616 B2
(45) Date of Patent: Jun. 25, 2019

(54) SYSTEM AND CIRCUIT FOR OBTAINING IMPEDANCE OR DIELECTRIC MEASUREMENTS OF A MATERIAL UNDER TEST

(71) Applicant: TransTech Systems, Inc., Latham, NY (US)

(72) Inventors: Frank H. Lipowitz, Rexford, NY (US); Adam Blot, Altamont, NY (US)

(73) Assignee: TRANSTECH SYSTEMS, INC., Latham, NY (US)

( * ) Notice: Subject to any disclaimer, the term of this patent is extended or adjusted under 35 U.S.C. 154(b) by 18 days.

(21) Appl. No.: 15/841,957

(22) Filed: Dec. 14, 2017

(65) Prior Publication Data
US 2018/0172612 A1 Jun. 21, 2018

Related U.S. Application Data

(60) Provisional application No. 62/434,789, filed on Dec. 15, 2016.

(51) Int. Cl.
G01N 27/02 (2006.01)
(52) U.S. Cl.
CPC .......... *G01N 27/026* (2013.01); *G01N 27/02* (2013.01); *G01N 27/028* (2013.01)

(58) Field of Classification Search
CPC ..... G01N 27/026; G01N 27/02; G01N 27/028
USPC .................................................. 324/601, 634
See application file for complete search history.

(56) References Cited

U.S. PATENT DOCUMENTS 5,397,993 A * 3/1995 Tews ...................... G01N 22/04
324/310

* cited by examiner

*Primary Examiner* — Farhana A Hoque
(74) *Attorney, Agent, or Firm* — Hoffman Warnick LLC

(57) ABSTRACT

Embodiments include a system and circuit for measuring characteristics of a material under test (MUT). In some cases, the system includes a circuit having level detectors to measure the change in strength between a reference signal and a return signal passed through the MUT. The system can include a computing device to evaluate the measured signals and adjust those signals within range of the level detectors and other circuit components. Circuits can include a time-of-flight digital convertor for determining the phase shift between the reference and return signals that pass through the MUT. The measured difference in signal strength and phase can be used to compute the complex impedance or dielectric properties of the MUT. This impedance or dielectric property can be correlated with a physical property of the MUT. The system may be operated at a single frequency, or over a range of frequencies.

20 Claims, 23 Drawing Sheets

System
100

BOARD CALIBRATION - 112

SHORT CIRCUIT ~0Ω

FIXED RESISTANCES, R

EQUIVALENT CIRCUIT FOR MODELING

ALTERNATE EQUIVALENT CIRCUIT FOR MODELING

SYSTEM AND CIRCUIT FOR OBTAINING IMPEDANCE OR DIELECTRIC MEASUREMENTS OF A MATERIAL UNDER TEST

TECHNICAL FIELD

The invention relates generally to systems, circuits and methods for determining characteristics of a material under test (MUT) using impedance or dielectric measurements of that MUT.

BACKGROUND

The use of impedance to measure the characteristics of construction, manufacturing, and biological materials by the application of impedance tomography and impedance spectroscopy is increasing.

The subject matter of U.S. Pat. No. 5,900,736, U.S. Pat. No. 6,414,497 and U.S. Pat. No. 7,219,024; US Patent Publication No. 2009/0270756; US Patent Publication No. 2012/0130212; US Patent No. 2013/0307564, Provisional U.S. Patent Application No. 61/703,488 (filed on Sep. 20, 2012); US Patent Publication No. 2014/0278300, US Patent Publication No. 2015/0137831; US Patent Publication No. 2015/0212026; Provisional U.S. Patent Application No. 62/039,204 (filed on Aug. 19, 2014); and Provisional U.S. Patent Application No. 62/103,835 (filed on Jan. 15, 2015) describe some impedance-related techniques for determining characteristics of materials, and are each incorporated by reference herein in its entirety.

SUMMARY

The system and circuit of the present subject matter relate to the measurement of the impedance of a MUT, as well as electronic devices and/or components for performing such measurements at a specific frequency or over a range of frequencies, with provisions for the self-adjustment of the transmit and reference signals to produce a measured signal within a desired range of the electronic measuring components over the frequency range, based upon the strength of the measured signal. The present subject matter provides an electronic circuit, a system, and a method to apply an electronic circuit which: 1) generates a transmit signal and a reference signal at a specific frequency or over a range of frequencies; 2) transmits a signal to a material under test (MUT) (which may include one or more sub-components); 3) compares the strength (and/or magnitude) of the transmitted signal passing through the MUT to the reference signal; 4) determines the phase relationship between the signal transmitted through the MUT relative to the reference signal; 5) computes the impedance or dielectric of the MUT (and in some cases, sub-components); and 6) applies the measured impedance or dielectric to characterize a physical property of the MUT. The approaches described herein can include characterization methods for the measuring circuit board and sensor system, as well as a method to gather data with the circuit board and sensor system.

Various embodiments of the disclosure relate generally to a system and circuit for the measurement of the impedance or dielectric of a material under test (MUT). In some cases, the system includes a circuit having level detectors to measure the change in strength between a reference signal and a transmit/receive (return) signal having passed through the MUT. The system can include at least one computing device configured to evaluate the measured signal levels and adjust those signals within range of the level detectors and other circuit components. Circuits according to various embodiments can include a phase determiner for determining the phase shift between the reference signal and the receive (return) signal that passes through the MUT. According to various embodiments, the measured difference in signal strength and phase are used to compute the complex impedance (or dielectric properties) of the MUT. This impedance or dielectric property can be correlated with a physical property of the MUT. The system may be operated at a single frequency, or over a range of frequencies.

In some particular embodiments, a system can include: a signal generator; a transmitting electrode connected with the signal generator and in electromagnetic communication with a material under test (MUT); a receiving electrode connected with the signal generator and in electromagnetic communication with the material under test (MUT); a reference level detector connected with the signal generator in parallel with the transmitting electrode; an absolute level detector and a phase determiner connected with the receiving electrode; a phase determiner connected with the receiving electrode and the signal generator; and at least one computing device connected with the signal generator, the phase determiner, the reference level detector, and the absolute level detector, the at least one computing device configured to: send a control signal to the signal generator to initiate: an transmit excitation signal to the MUT via the transmitting electrode at a selected frequency, and a reference signal to the reference level detector; receive a reference level signal from the reference level detector; receive a return signal from the MUT via the receiving electrode and the absolute level detector; receive a phase signal from the phase determiner; and record the reference level signal, the phase signal and the return signal.

In some particular embodiments, the phase determiner includes a means to generate a comparison signal at the same frequency as the reference and transmitting frequency but with varying phase shifts relative to reference and transmit signals. This comparison signal is superimposed on or summed with the receive signal. The phase of the comparison signal which, when superimposed on the receive signal, produces the peak voltage defines the value phase shift.

In one embodiment, the phase determiner uses a time-of-flight method with a Time-to-Digital Conversion (TDC) chip to directly measure the time between edges on the comparison and receive (return) signals. This measured time may be used to compute the phase shift between the two signals.

In some cases, a system can include: an electromagnetic signal generator operating at a fixed frequency or over a range of frequencies generating two parallel signals, a Reference Signal and a Transmit Signal; a transmitting electrode connected with the Transmit Signal from the signal generator and in electromagnetic communication with a material under test (MUT); a receiving electrode connected in electromagnetic communication with the material under test (MUT) generates a Receive Signal; a reference absolute level detector connected with the Reference Signal from the signal generator; a receive absolute level detector connected with the Receive Signal from the receiving electrode; a time-of-flight phase determiner means connected with the Receive Signal from the receiving electrode and the Reference Signal from the signal generator; and at least one computing device connected with the signal generator, the phase determiner, the reference absolute level detector, and the receive absolute level detector, the at least one computing device configured to: send a control signal to the signal generator to initiate: an excitation signal to the MUT via the transmitting electrode at a selected frequency or over a range of frequencies, and a reference signal to the reference absolute level detector; receive a reference level signal from the reference absolute level detector; receive a return Receive Signal from the MUT via the receiving electrode and the absolute level detector; receive a phase signal from the phase determiner; and record the Reference Signal level, the phase signal, and the Receive Signal level.

In certain cases, the at least one computing device is further configured to use the signal levels and phase angle to compute either the impedance or dielectric of the MUT to determine a physical characteristic of the MUT.

In particular embodiments, the physical characteristic includes at least one of density, water content, or physical composition.

In some embodiments, the system further includes a set of circuit board terminals connecting the circuit board with the transmitting electrode and the receiving electrode; and a calibration circuit conductively coupled with the circuit board terminals, the calibration circuit configured to short circuit across the circuit board terminals, wherein the at least one computing device is further configured to: generate a calibration signal across the calibration circuit; receive and compare the calibration signal absolute level reading to the Reference Signal absolute level reading; and modify the control signal to the signal generator in response to the calibration signal deviating from the reference level signal by greater than a threshold.

In certain embodiments, the threshold is equal to approximately a one percent deviation.

In particular embodiments modifying the control signal to the transmit amplifier includes providing instructions to adjust the excitation signal to the transmitting electrode by an amount corresponding with the deviation between the calibration signal and the Reference Signal.

In some cases, the system further includes a transmit amplifier connected with and located between the signal generator and the transmitting electrode, the transmit amplifier for amplifying the excitation signal prior to transmission into the MUT.

In certain instances, the system further includes a fixed level attenuator connected with and located between the signal generator and the reference absolute level detector, wherein the fixed level attenuator is configured to decrease in amplitude of the Reference Signal to approach an amplitude of the Receive Signal.

In particular embodiments, the system further includes: a set of circuit board terminals connecting the circuit board with the transmitting electrode and the receiving electrode; and a calibration circuit conductively coupled with the circuit board terminals, the calibration circuit configured to apply at least one of a resistive or a capacitive load across the set of circuit board terminals, wherein the at least one computing device is further configured to: generate a calibration signal across the calibration circuit; receive and compare the calibration signal absolute level reading to the Reference Signal absolute level reading; and modify the control signal to the signal generator in response to the calibration signal deviating from the reference level signal by greater than a threshold.

In certain cases, applying the at least one of the resistive or the capacitive load includes applying both the resistive load and the capacitive load across the set of circuit board terminals, wherein the resistive load and the capacitive load are selected based upon an emulated impedance of the MUT.

In some embodiments, the at least one computing device is further configured to: iteratively send a control signal to the transmit amplifier to adjust a gain on the transmit amplifier until the calibration signal deviates from the reference absolute level signal by less than or equal to the threshold.

In certain implementations, the at least one computing device is further configured to: store an amplification value corresponding with the calibration signal deviating from the reference signal by less than or equal to the threshold.

In particular cases, the at least one computing device is further configured to: store a corresponding phase angle for the reference signal and the receive signal at the amplification value, received from the phase determiner.

In some embodiments, the system further includes an MUT calibration circuit electromagnetically coupled with the transmit electrode and the receive electrode, the MUT calibration circuit configured to emulate an impedance response of the MUT at the receive electrode, wherein the at least one computing device is further configured to: generate a calibration signal across the calibration circuit; receive and compare the calibration signal absolute level reading to the Reference Signal absolute level reading; and modify the control signal to the signal generator in response to the calibration signal deviating from the reference level signal by greater than a threshold.

In certain instances, the calibration circuit includes an equivalent electrode array configured to emulate the impedance response of the MUT that is electromagnetically coupled to the transmit electrode and the receive electrode.

In particular embodiments, the at least one computing device is further configured to: iteratively send a control signal to the transmit amplifier to adjust a gain on the transmit amplifier until the calibration signal deviates from the reference absolute level signal by less than or equal to the threshold.

In some cases, the at least one computing device is further configured to: store a transmit amplification value corresponding with the calibration signal deviating from the Reference Signal by less than or equal to the threshold.

In certain implementations, the at least one computing device is further configured to: store a corresponding phase angle between the Reference Signal and the Receive Signal at the amplification value, received from the phase determiner.

In particular cases, the at least one computing device is further configured to: iteratively send a control signal to the phase determiner amplifier to adjust a gain on the amplifier until the receive signal and the reference signal levels are within an operating range of the edge detector of the phase determiner.

In some embodiments, the at least one computing device is further configured to: store a phase angle of the control signal corresponding with the return signal and the reference level signal being within the operating range of the phase determiner.

In certain implementations, the signal generator includes a direct digital synthesizer and a signal conditioner.

In particular instances, the absolute level detector provides an analog value of an absolute magnitude of a voltage of the reference signal to the at least one computing device.

In some cases, the system further includes a time-of-flight phase determiner means connecting the Reference Signal and Receive Signal to an edge detector which converts the sinusoidal signals to a square waves which are then processed by a Time-to-Digital Conversion chip which provides a precision measurement of the time between the edges of the two waves.

In particular cases, the at least one computing device is further configured to compute the phase angle between the Reference Signal and the Receive Signal by the following equation:

$$\text{Phase Angle} = 360 \times (\text{Phase Time}/\text{Cycle Time}).$$

DETAILED DESCRIPTION

The various methods and procedures described here are related to the determination of the impedance characteristics of a material under test (MUT) at a single selected frequency. A single frequency is adequate for tomographic analysis as described in US Patent Publication Nos. 2010/037361, 20130307564, and 2015/0137831, and U.S. Patent Application No. 61/703,488; and or for the determination of physical properties of selected materials that act as pure capacitors, such as hot mix asphalt, as described in U.S. Pat. Nos. 5,900,736 and 6,414,497. Each of these applications, publications and issued patents are hereby incorporated by reference in its entirety.

Figure 1:
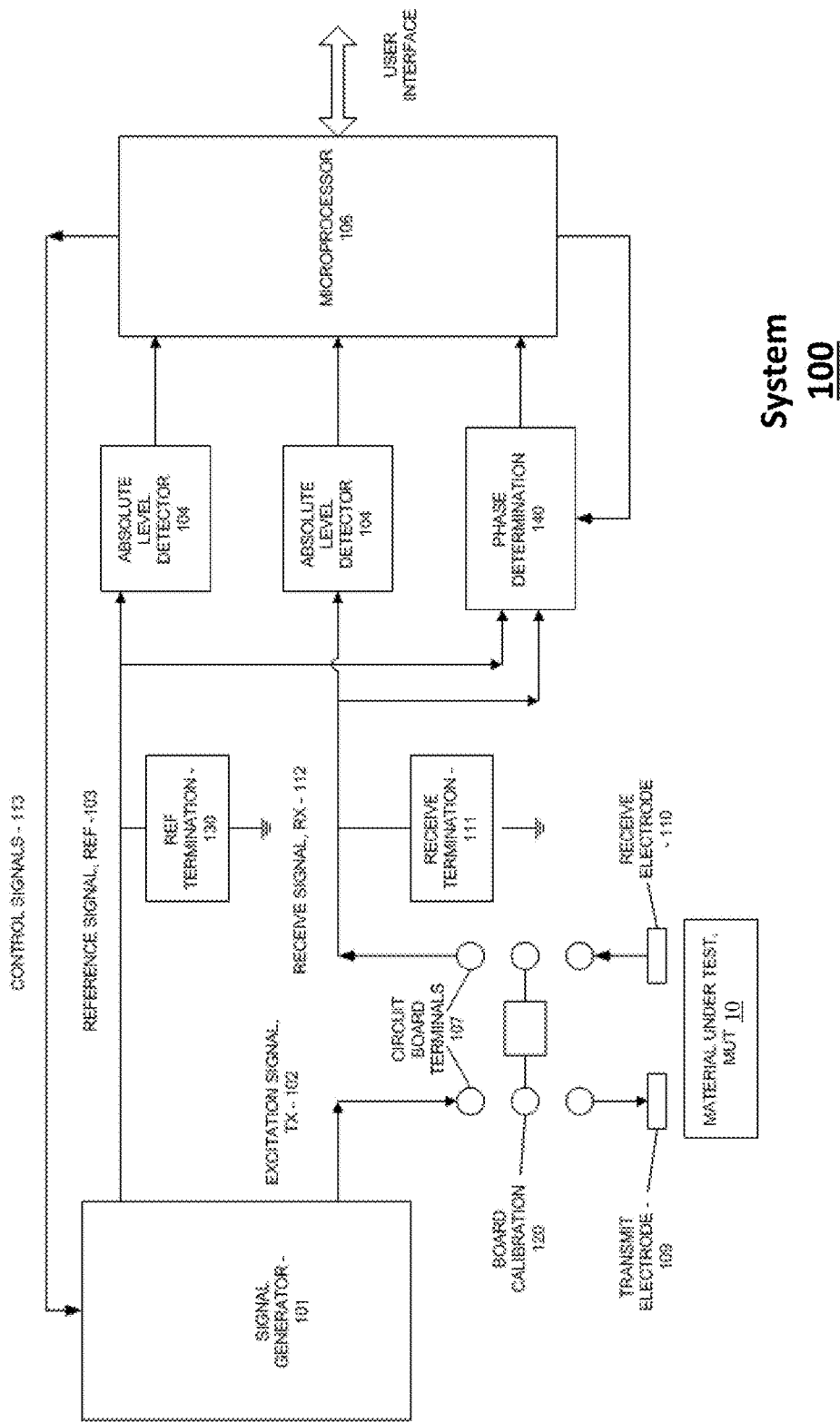
FIG. 1 shows a general configuration of a sensor system including an impedance measurement circuit according to various embodiments of the disclosure.

An illustrative schematic view of a system 100 according to various embodiments is illustrated in FIG. 1. The MUT 10 is in electromagnetic communication with an array of electrodes, 109 and 110. The electromagnetic communication may be either electrically conductive or electrically non-conductive, and in some cases electrodes 109, 110 are separated from a surface of MUT 10 by a distance (or, off-set). In the following discussions the non-conductive application will be discussed in relatively greater detail. According to various embodiments, an electromagnetic signal is generated by a signal generator 101, triggered by a control signal 113 from a microprocessor 106. In many cases, two signals are transmitted from signal generator 101. One signal is a reference signal 103, which is transmitted to a level detector 104, the output of which is transmitted as an analog voltage level signal to microprocessor 106. The microprocessor 106 selected can have a 12-bit A-to-D input port. The other signal, excitation signal (TX102) or "transmit" signal, is transmitted to a circuit board terminal 107, on a circuit board that is electrically coupled with the transmitting (sensor) electrode 109. After passing through MUT 10, the transmitted signal is received by the receiving (sensor) electrode 110, which is electrically coupled with the circuit board through terminal(s) 107. From the circuit board terminals 107, a receive signal 112 is transmitted to a level detector 104, the output of which is transmitted as an analog voltage level signal to microprocessor 106. In various embodiments, the levels of the reference signals 103 and receive signals 112 can be recorded by microprocessor 106 and stored for subsequent use/combination with the phase angle between the reference signal 103 and receive signal 112, in order to compute the impedance and/or dielectric value of the MUT 10. This then can be correlated with a desired physical property of the MUT 10 (such as density for asphalt). A circuit board level calibration component 120 is also shown, and is discussed further herein.

Figure 2:
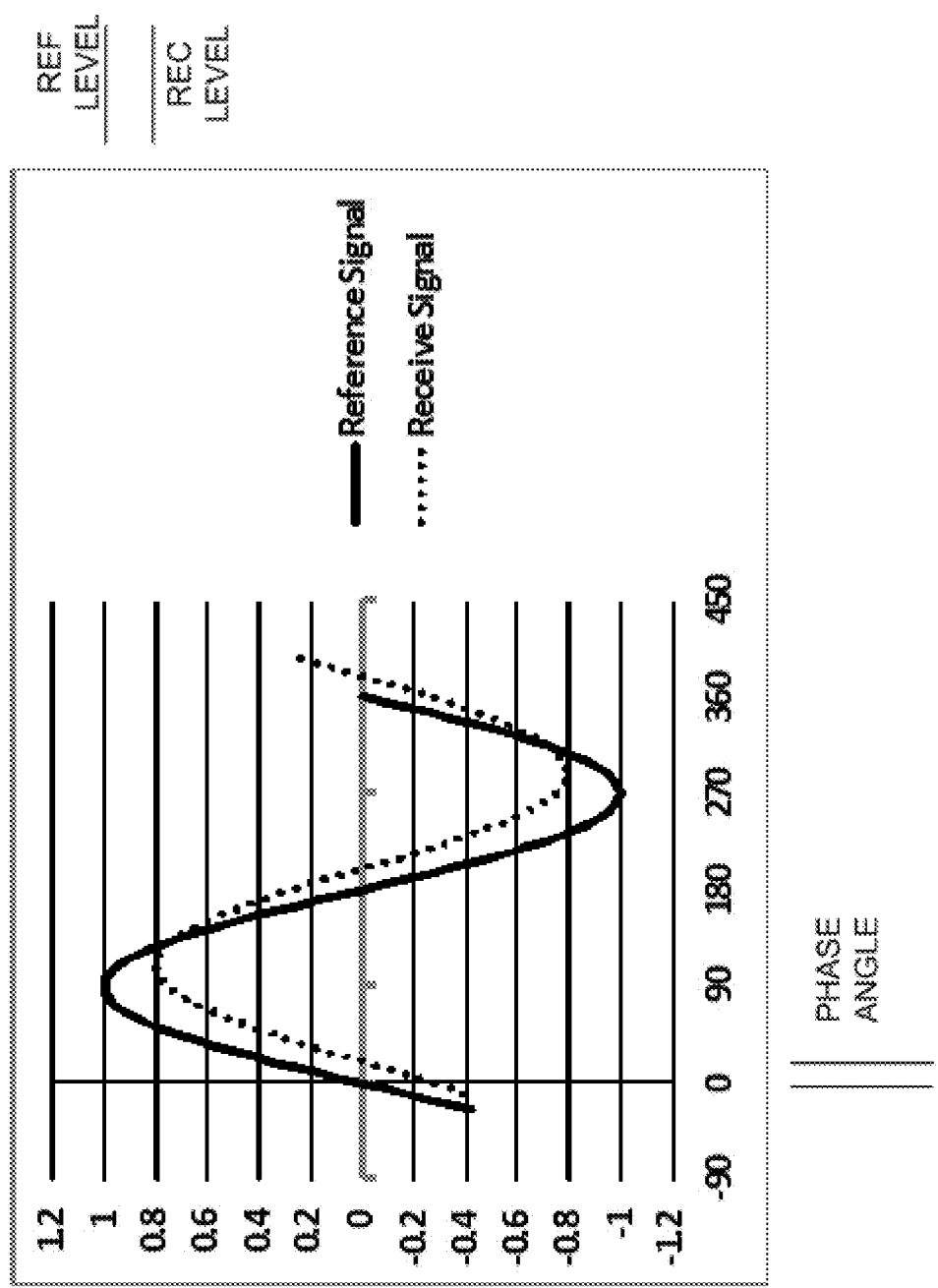
FIG. 2 shows an example graphical depiction of the signal differences of reference signals and return signals from the sensor system of FIG. 1 according to various embodiments of the disclosure.

Basic quantities measured at a given frequency can include the change in the magnitude between the reference signal (level) 103 and the received signal (level) 112, due, for example, to the resistive dissipation of the signal as it passes through MUT 10; and the phase shift of the received signal 112 relative to the reference signal 103, due to, for example, capacitive effects of the MUT 10. In general, physical materials may not produce detectable inductive losses without specifically setting tests to induce such losses (which may be feasible with only certain classes of materials). FIG. 2 illustrates the effects passing reference signal 103 through MUT 10 has on received signal 112. The differences between reference signal 103 and receive signal 112 are discussed further herein.

While the system(s) disclosed herein may include various conventional components, as well as configurations specific to the aspects of the disclosure, it is understood that components may be included in the design of the circuit to achieve different operational characteristics without affecting the scope of the operation of the system(s).

Figure 3:
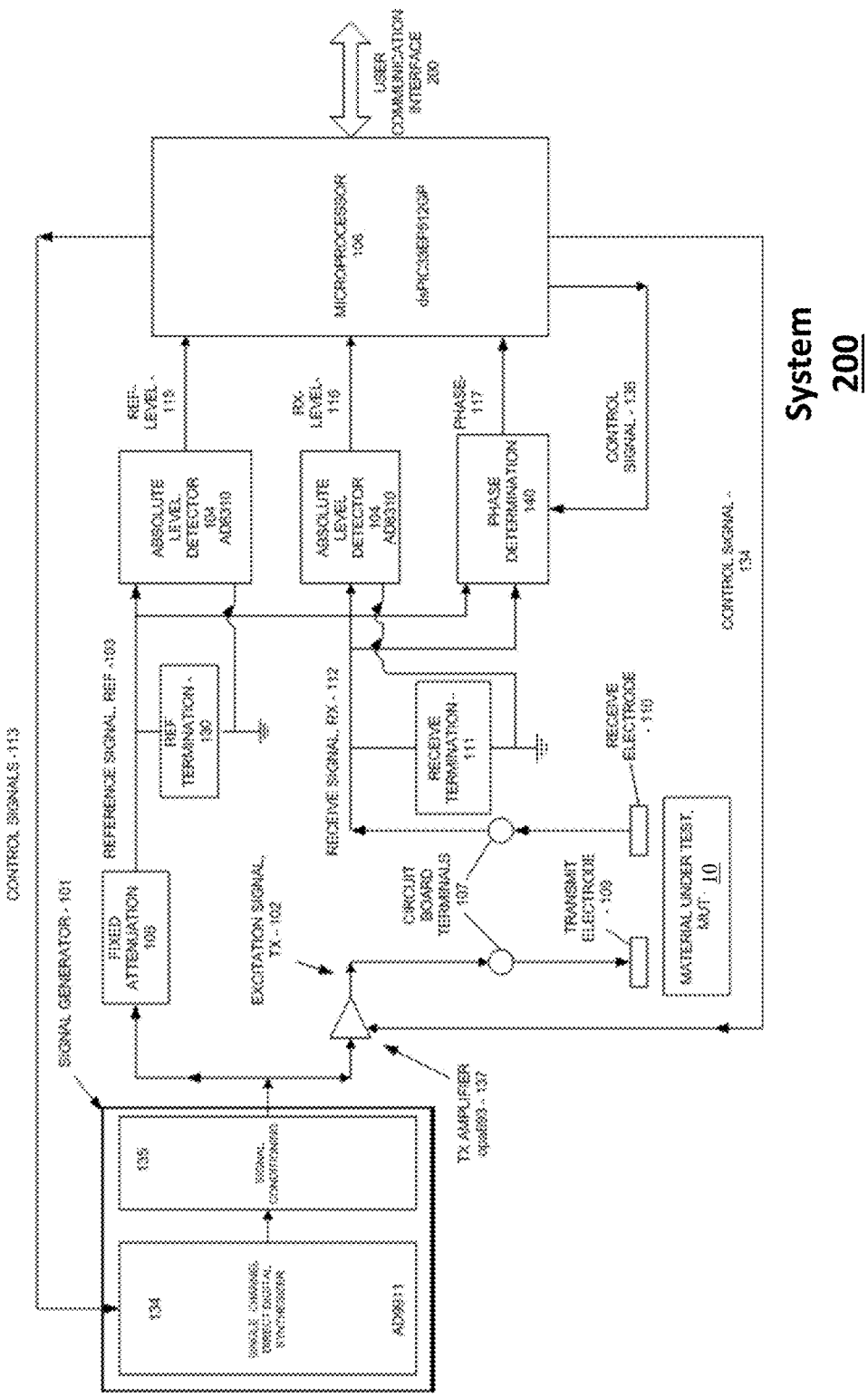
FIG. 3 shows a particular configuration of the sensor system of FIG. 1 according to various embodiments of the disclosure.

Turning to FIG. 3, an additional system 200 according to various embodiments is shown schematically. Common elements between the figures can represent substantially common components. As shown in FIG. 3, system 200 can include a signal generator 101 which can include a single channel Direct Digital Synthesizer (DDS) (such as the Analog Devices AD 9911) 134, in some embodiments. In various embodiments, coupled with the DDS 134 is a signal conditioner 135 configured to condition the control signal 113 prior to splitting that signal between a reference signal 103, and an excitation signal 102. In some embodiment, reference signal 103 is passed through a specified fixed level attenuator 108, and then split again with one leg going to a phase determiner 140, and another leg going to an absolute level detector 104 (e.g., an AD8310) with a reference termination 130, known in the art. Absolute level detector 104 can produce an analog value of the absolute magnitude of the voltage of reference signal 103. This analog value may act as an input to microprocessor 106, e.g., at a 12-bit A-to-D port (e.g., a Microchip dsPIC33EP512GP).

The second leg of the signal from signal conditioner 135 passes through an amplifier, 137 as excitation signal 102, to a terminal 107 on the circuit board, connected to a transmit (sensor) electrode, 109. The transmit electrode 109 and the receive electrode, 110, are configured to electromagnetically communicate with MUT 10. Electromagnetic communication between the electrodes 109, 110 and MUT 10 may be either electrically conducting or electrically non-conducting, as shown in FIG. 3. Receive electrode 110 is connected to circuit board terminal 107, and receives a response signal (receive signal 112) from MUT 10. From the terminal 107, the receive signal 112 is split between a leg going to the phase determiner 140, and an absolute level detector 104, with a Reference Termination 111, known in the art. Absolute level detector produces an analog value of the absolute magnitude of the voltage of the reference signal 112. This analog value may act as another input to microprocessor 106, e.g., at a second 12-bit A-to-D port. At this point, reference signal 103 and the receive signal 112 received at phase determiner 140 is passed as a digital value of the time between trigger points of the reference signal 103 and receive signal 112, shown as phase 117. This digital time value of phase 117 can be inputted to microprocessor 106, and stored in some cases. As shown DDS 134 can be controlled by microprocessor 106, e.g., through control signal 113, by specifying the frequency and amplitude of the signal generated by DDS 134.

In various embodiments the fixed level attenuator 108 can minimize the amount that the TX Amplifier 137 needs to amplify the excitation signal 102 as it passes through MUT 10, so that both receive signal 112 and attenuated reference signal 103 are within the dynamic range of the absolute level detectors 104.

Figure 4:
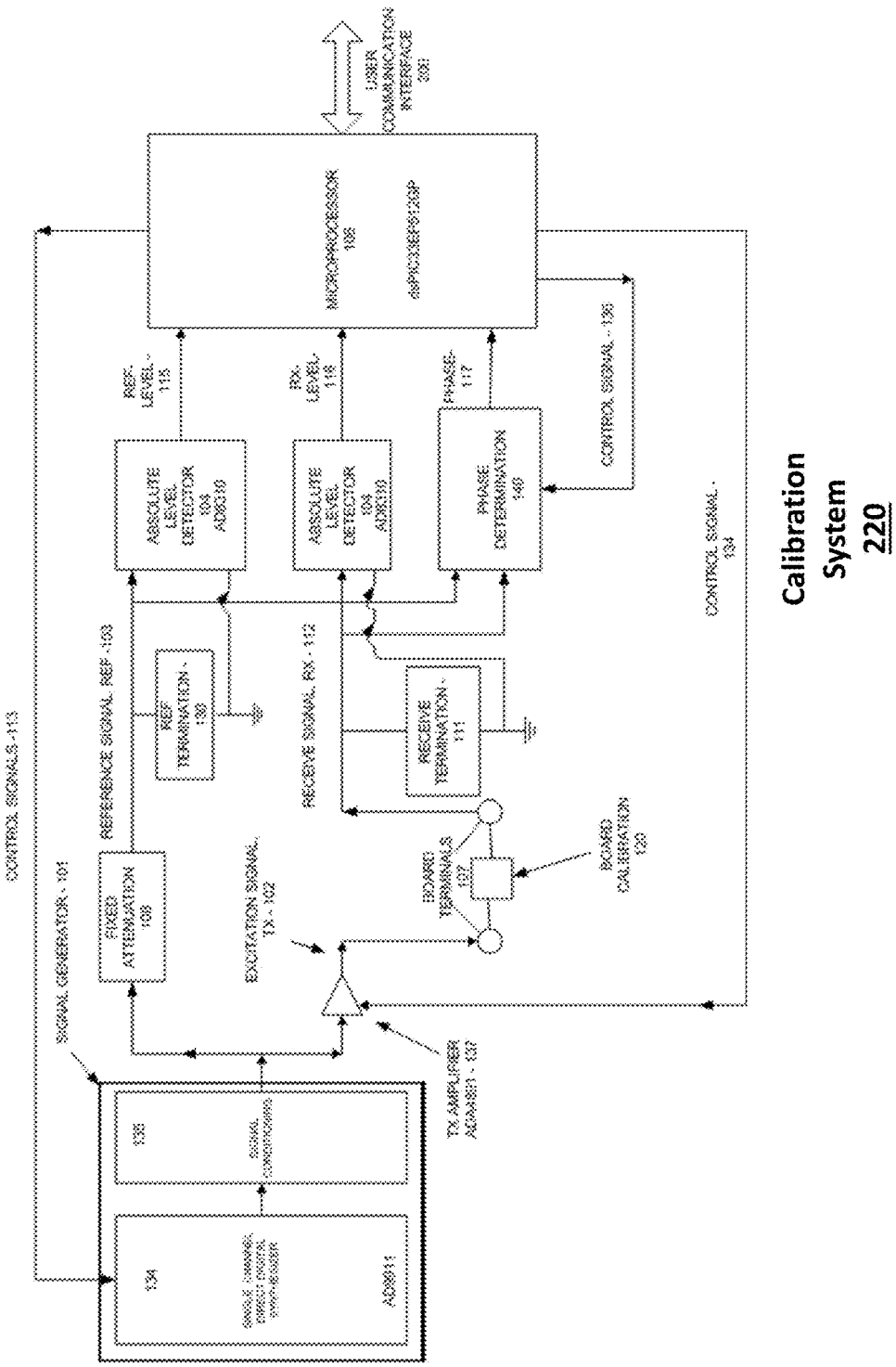
FIG. 4 shows a calibration system according to various embodiments of the disclosure.
Figure 5:
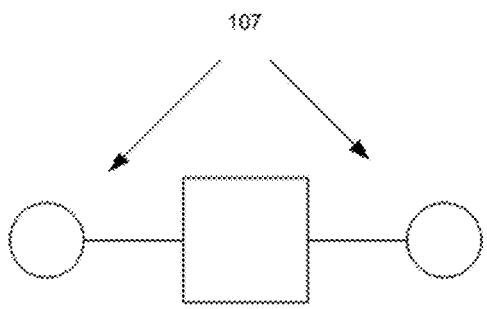
FIG. 5 illustrates several equivalent circuit models compatible with the calibration system of FIG. 4.
Figure 5:
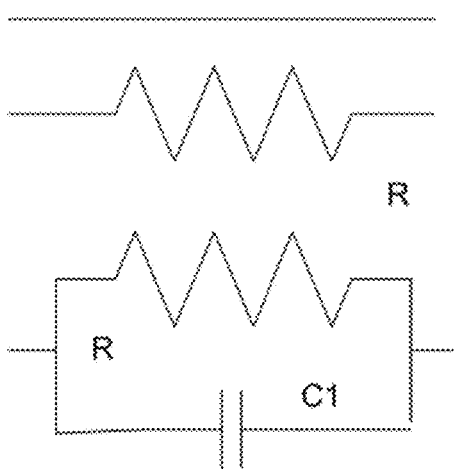
Figure 5:
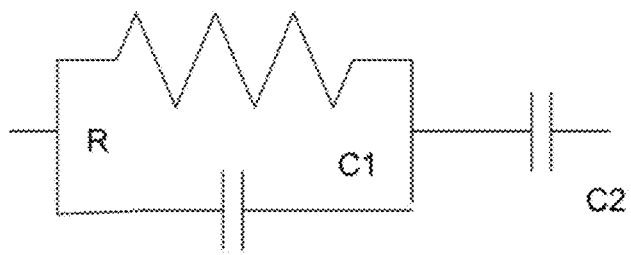
Figure 6:
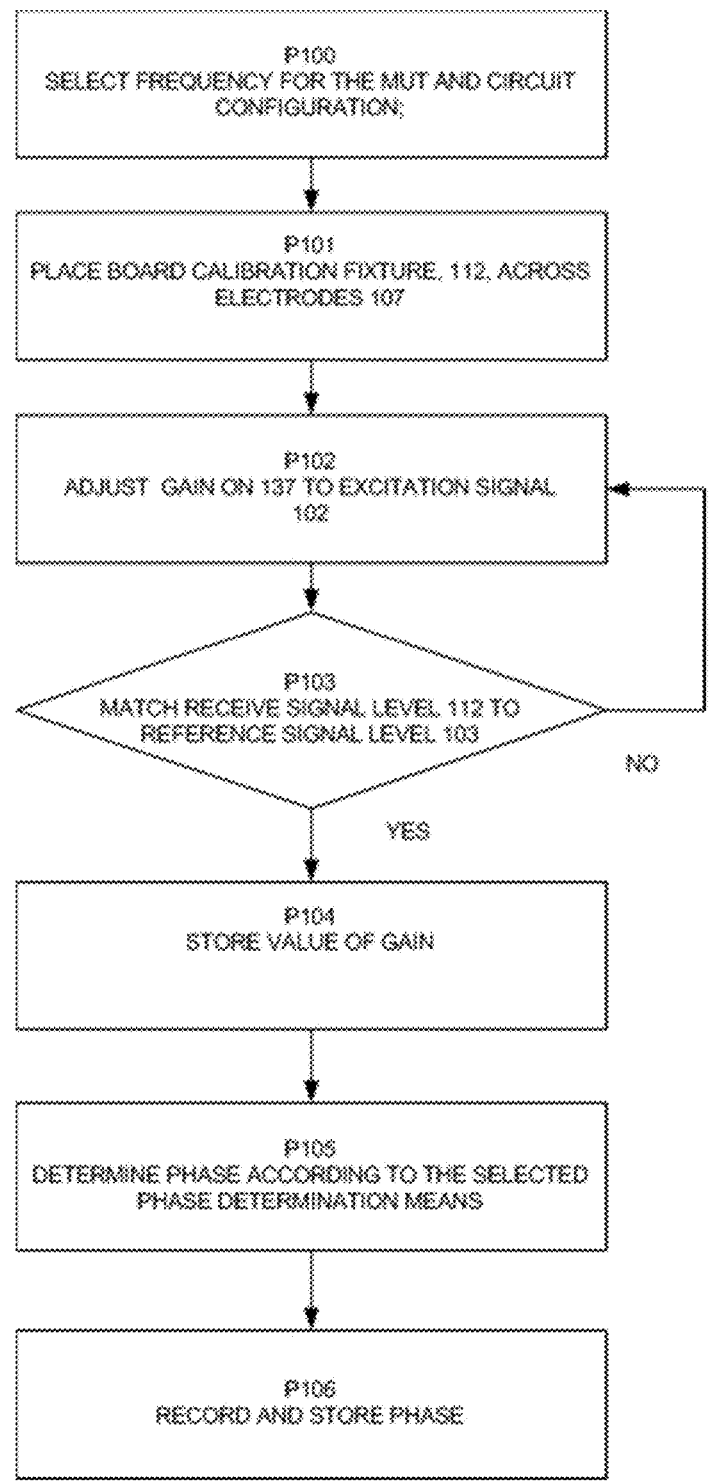
FIG. 6 shows a flow diagram illustrating processes in a method according to various embodiments of the disclosure.

In various embodiments, in order for the system to calibrate the circuit board, the voltage difference between the reference signal 103 and receive signal 112 are eliminated, without MUT 10 at the board level and the sensor system level. This is accomplished by using a "short" for the board calibration 120 (as illustrated in FIG. 4), and adjusting the TX amplifier 137, so that the RX Level 116, equals the REF Level 115. Also, in some cases, the phase difference between reference signal 103 and receive signal 112 are known at the board level and the sensor system level. Approaches for standardizing or calibrating system 200 are described with respect to calibration system 220, illustrated schematically in FIG. 4. As compared with system 200, calibration system 220 further includes a board calibrator 120 located between the terminals 107 of the circuit board. FIG. 5 illustrates further schematic details of board calibrator 120, in several calibration scenarios. A first configuration, as shown, is to "short" the two electrodes. By "shorting," a conductor is placed between the electrodes 107. However, the use of a "short" with this configuration of the board circuit will not be effective due to the presence of attenuator 108 (FIG. 4). In order to characterize the circuit board, a resistive or capacitive load is applied as shown in FIG. 5. Another approach is to use a combination of resistive and capacitive loads (as shown in FIG. 5) that emulate the approximate impedance characteristic of the MUT. In general, the range of the expected impedance characteristics of the MUT 10 at a given frequency is known, as this would be a requirement for the effective design of the sensor circuit. For examples, if the MUT 10 is hot mix asphalt, it is known in the art that this material acts as a pure capacitor with a dielectric value in the range of 4 to 7, depending on the degree of compaction. Soils used in construction also have a defined range of dielectric depending on soil type, moisture level, and degree of compaction. Therefore, using a Resistor-Capacitor (RC) circuit within the range of the impedance characteristics of the MUT (e.g. asphalt), or a series of RC circuits that cover the range of the impedance characteristics of the MUT (e.g. soil), can provide a characterization of the variations of the individual components of the system 200 (FIG. 3) and their distortions of the signals in the system 200 as a whole. FIG. 6 presents a characterization or calibration procedure for system 200 (FIG. 3). Referring to calibration system 220 in FIG. 4 and the process in FIG. 6 collectively, processes can include:

P100: Select a transmission frequency at electrodes (transmit electrode(s) 109) specific to the type of MUT 10 being tested with the configuration of system 200 (for example, in general, a frequency in the range of 10 MHz to 20 MHz is acceptable with materials encountered in civil construction projects);

P101: Place the selected board calibrator 120 (see FIG. 5), appropriate simulated impedance(s) for the specific MUT 10 across terminals 107, and initiate the control signal 113 to DDS 134, to generate the signal at the selected frequency and voltage level;

P102: Adjust the gain on amplifier 137 (via control signal 113 from microprocessor 106);

P103: If the RX Level 116 does not equal the REF level 115, adjust the amplifier 137 accordingly until the RX level 116 and REF level 115 are identical;

P104: Store the value of the amplification from amplifier 137 at microprocessor 106, UCI 200 or other data storage device;

P105: Determine the phase angle between the REF level 115 and RX signal 116 according to the selected phase determiner 140; and P106: Record and store the measured phase angle from phase determiner 140, e.g., at microprocessor 106, UCI 200 or other data storage device. Various aspects of the phase determiner 140 are discussed in detail further herein.

Having characterized/calibrated system 200, sensors (electrodes 109, 110) and their associated connectors, as well as an air gap or an insulator layer (optional) between electrodes 109, 110 and MUT 10, e.g., for a non-conducting electromagnetic communication with MUT 10, may be added. Additionally, after characterizing/calibrating system 200, impedance characteristics of the MUT 10 can be calculated, e.g., using an equivalent circuit model with a combination of resistors and capacitors in series and/or parallel arrangements. That is, electrodes 109, 110 can be used to obtain data used to calculate a complex impedance, Z, of each component in the measured structure. This is illustrated schematically in FIG. 7. The circuit board is configured to measure ZM, which is a function of the impedances of all of the individual components of the measured structure (e.g., terminals 107, electrodes 109, 110, air gap and MUT 10):

$$ZM=f(Z1,Z2,Z3,Z4,Z5,Z6,Z7)$$

A target measurement for MUT 10 is Z4. That is, an objective of the characterization procedure outlined in FIG. 6 is to assure that the effects of the impedances Z1 and Z7 at the terminals 107, which include the effects of all the measured structure components and the circuit design of the board, can be ignored in determining the value of Z4, attributable to MUT 10. However, it still may be difficult to transition from the measured impedance at terminals 107 to the impedance of MUT 10. If the characterization or calibration is performed at the level where the electrodes are placed into electromagnetic communication with the MUT 10, the point of the measured impedance is now moved to the electrode/air-insulator (or electrode 109,110/MUT 10) interface. This simplified scenario is shown schematically in FIG. 8 where the sensor characterization now occurs at the sensor electrodes 109 and 110. In this case, the measured impedance, ZMS, is just the sum of the impedance of the two air gaps between electrodes 109, 110 and MUT 10 (or another insulator), and the MUT 10:

$$ZMS=Z3+Z4+Z5$$

Figure 7:
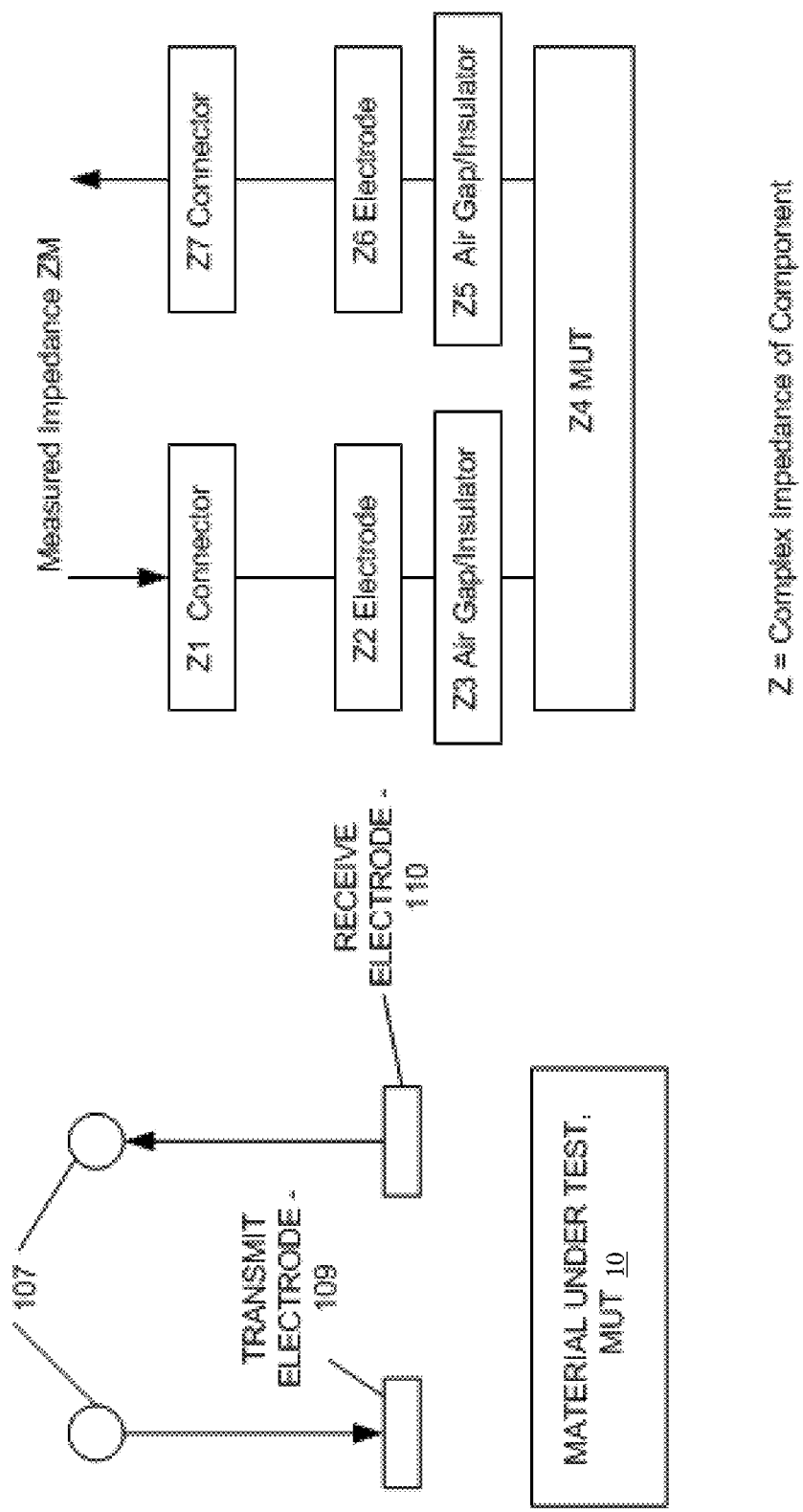
FIG. 7 shows an equivalent circuit model for the calibration system 220 of FIG. 4 according to various embodiments of the disclosure.

Solving for Z4 becomes much simpler in this approach when compared with the configuration in FIG. 7.

Figure 8:
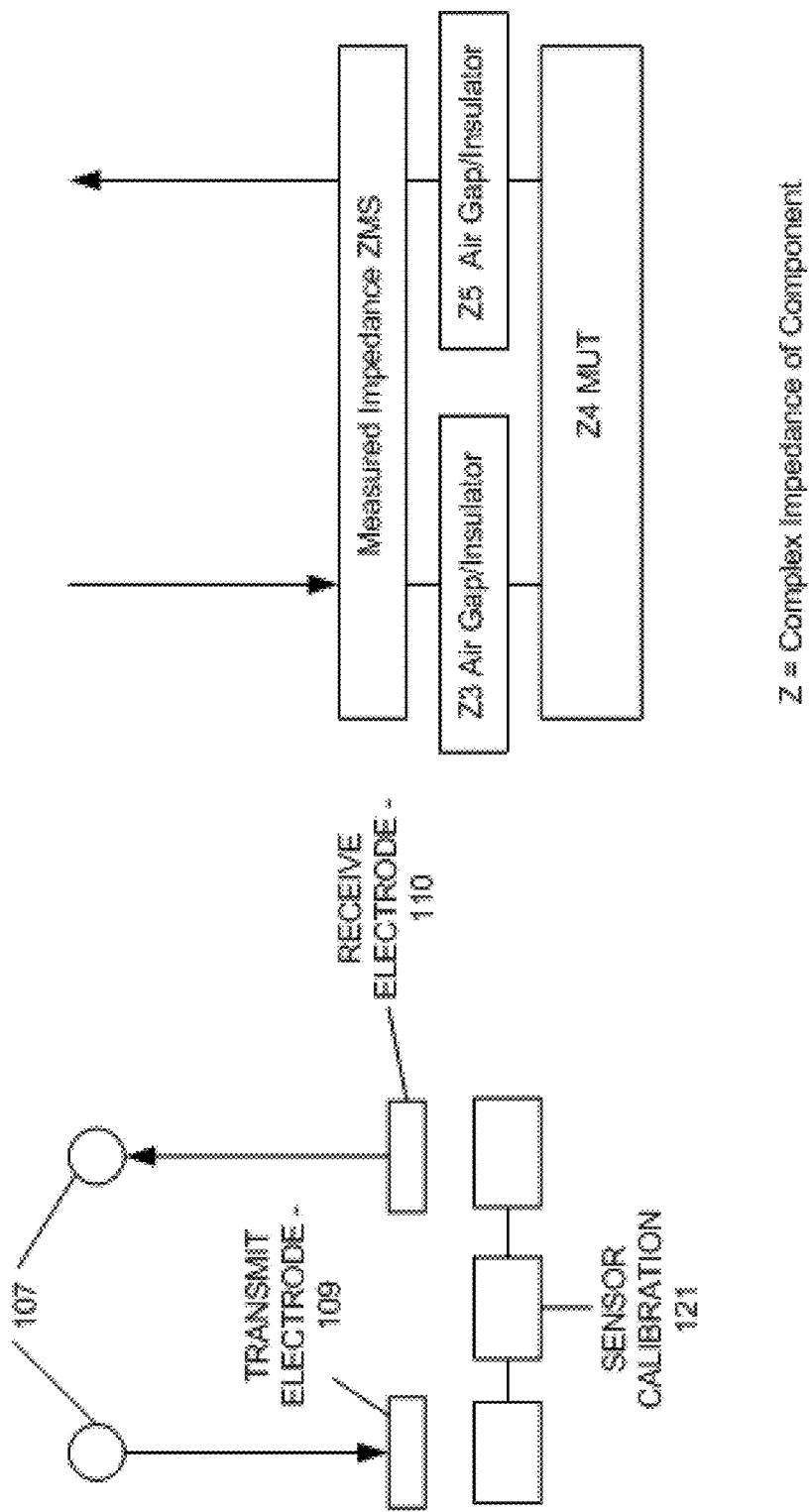
FIG. 8 shows an equivalent circuit model for the calibration system 220 of FIG. 4 according to various embodiments of the disclosure.
Figure 9:
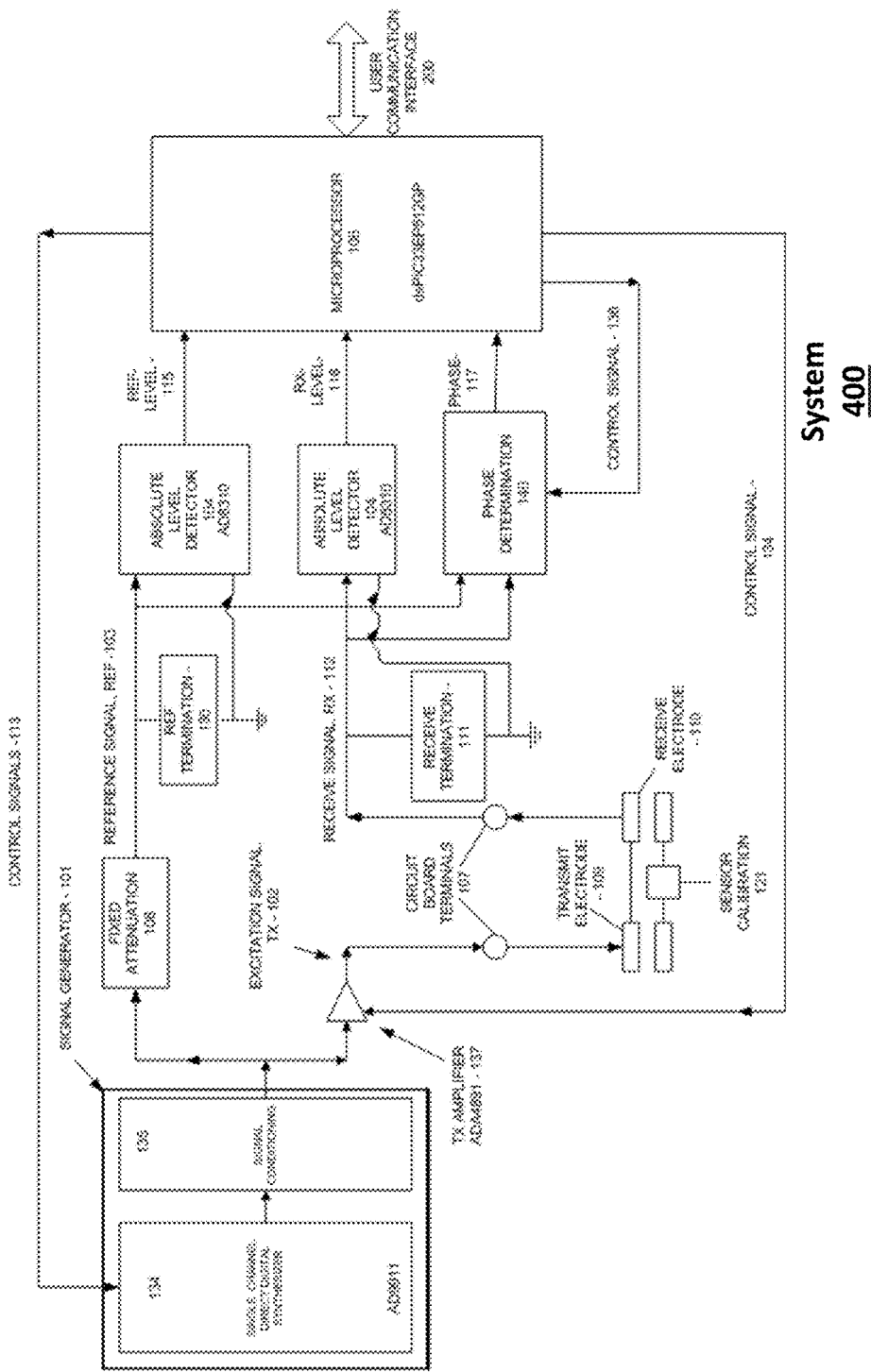
FIG. 9 shows a sensor system including a calibration fixture at the sensor system level according to various embodiments of the disclosure.
Figure 10:
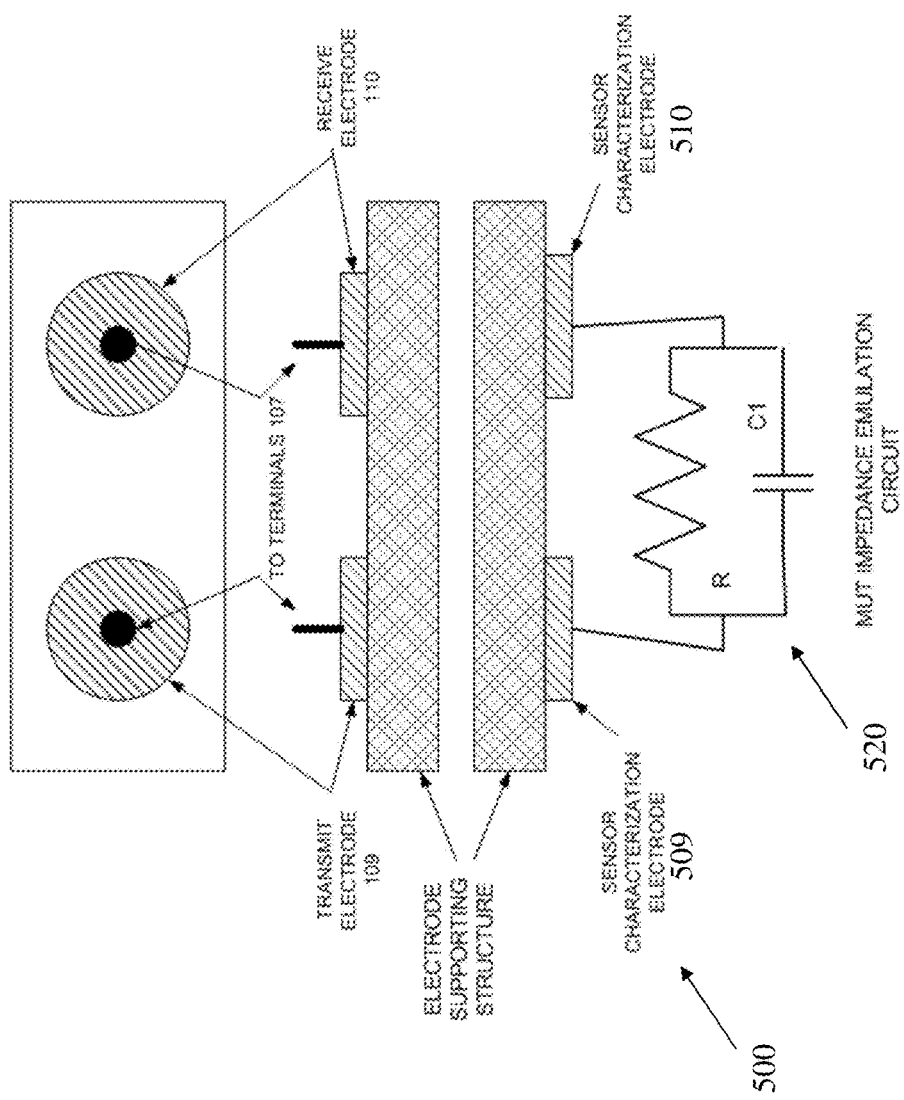
FIG. 10 is a schematic depiction of sensor calibration fixtures and equivalent circuit models for the system of FIG. 9, according to various embodiments of the disclosure.

The characterization or calibration of the system 200 may be performed in a similar manner as described with respect to the circuit board herein. FIGS. 8 and 9 illustrate components in an additional calibration system 400, which utilizes a sensor calibrator 121 being placed across the sensor electrodes 109 and 110. The equivalent RC circuit of the sensor calibrator 121 is similar to that used to emulate the impedance characteristics of MUT 10 with board calibrator 120 shown in FIG. 5. However, as illustrated in FIG. 10, rather than having a wire contact to the electrodes 109, 110, an equivalent electrode array 500 is used to provide electromagnetic wave-based communication that better characterizes the electromagnetic communication between electrodes 109, 110 and MUT 10. In FIG. 10, circular (e.g., copper) electrodes are shown as examples of electrodes 109, 110, and may be mounted on a support structure, typically a circuit board material such as FR4 or G9 (glass reinforced epoxy laminate sheets). Other electrode shapes and materials are also possible, and other support structure materials are also possible. According to various embodiments, sensor calibrator 121 includes the sensor characterization electrodes 509, 510, which oppose electrodes 109, 110. As described herein, electrodes 109, 110 are connected to the board terminals 107. The sensor characterization electrodes 509, 510 are connected to an MUT impedance emulation circuit 520, which is configured to emulate the impedance of one or more particular types of MUT 10.

An active version of an impedance emulator is presented in US Patent Publication No. 2014/0278300. This device varies the emulated impedance over a range of frequencies.

Figure 11:
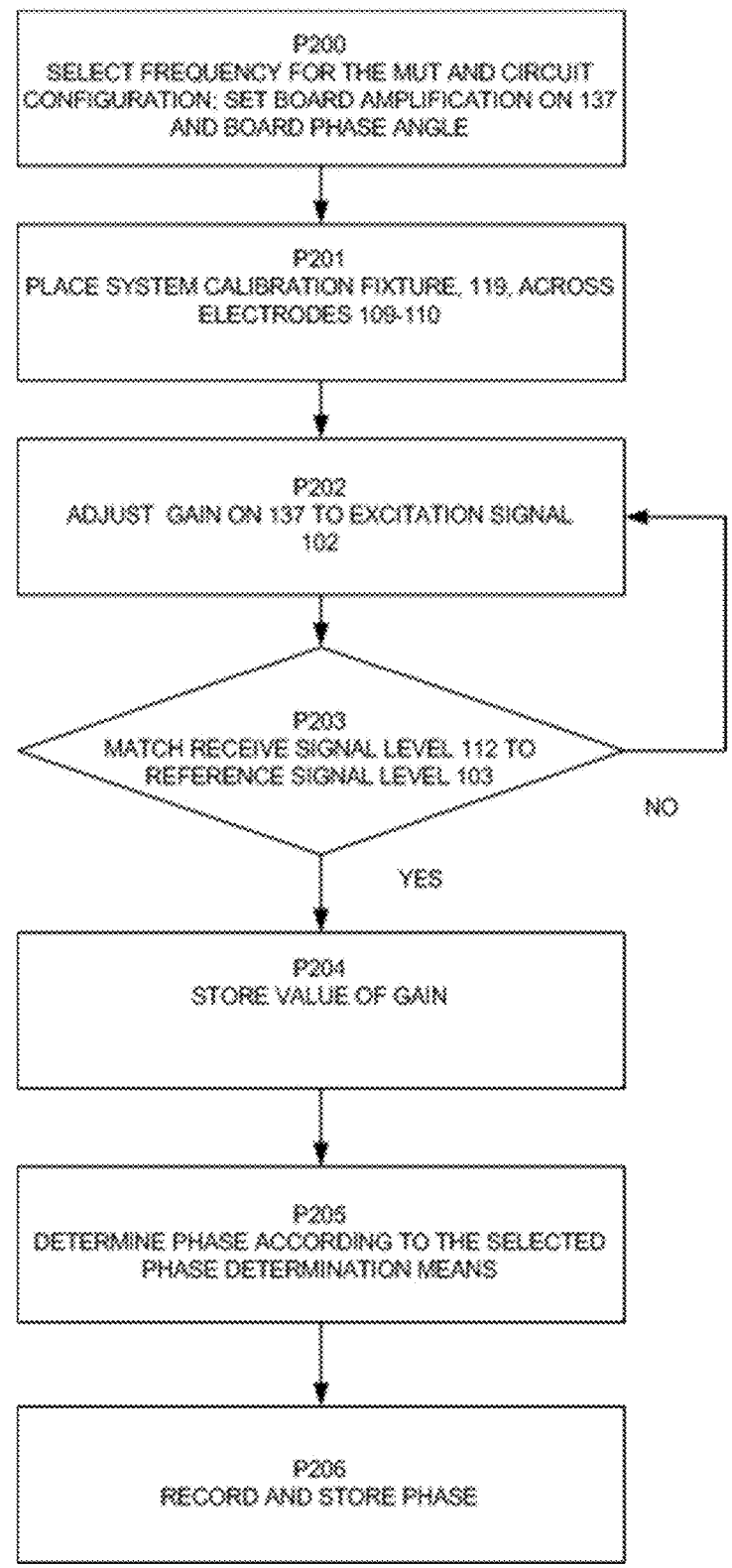
FIG. 11 shows a flow diagram illustrating a method according to various embodiments of the disclosure.

FIG. 11 presents a flow diagram illustrating a standardization/calibration process which may be used in conjunction with system 400 (FIG. 9), including equivalent electrode array 500 (FIG. 10). Referring to FIGS. 9-11, the process may include the following sub-processes:

P200: Select a frequency specific for the MUT 10 being tested with the selected circuit board configuration (e.g., for tomographic measurements, frequencies in the range of 10 MHz to 20 MHz are generally acceptable; e.g., for spectrographic measurements, such as for soils, frequencies in the range of 10 MHz to 50 MHz are used as described in U.S. Pat. No. 7,219,024);

P201: Place the selected sensor calibration fixture 121 (FIG. 9), appropriate for the simulated impedance(s) of the specific MUT 10, in electromagnetic communication with electrodes 109, 110 and initiate the control signal 113 to DDS 134, to generate excitation signal 102 at the selected frequency and voltage level determined in process P200;

P202: Adjust the gain on amplifier 137 (FIG. 9) (via control signal 134 from microprocessor 106);

P203: If the RX level 116, does not equal REF Level 115, adjust amplifier 137 accordingly until the RX level 116 and REF level 115 are approximately (+/−one percent) identical;

P204: Store the value of the amplification from amplifier 137 at microprocessor 106, UCI 200 or other data storage device;

P205: Determine the phase angle between the REF level signal 115 and RX level signal 116 according to the selected phase determiner 140; and P206: Record and store the measured phase angle 117 at microprocessor 106, UCI 200 or other data storage device.

Figure 12:
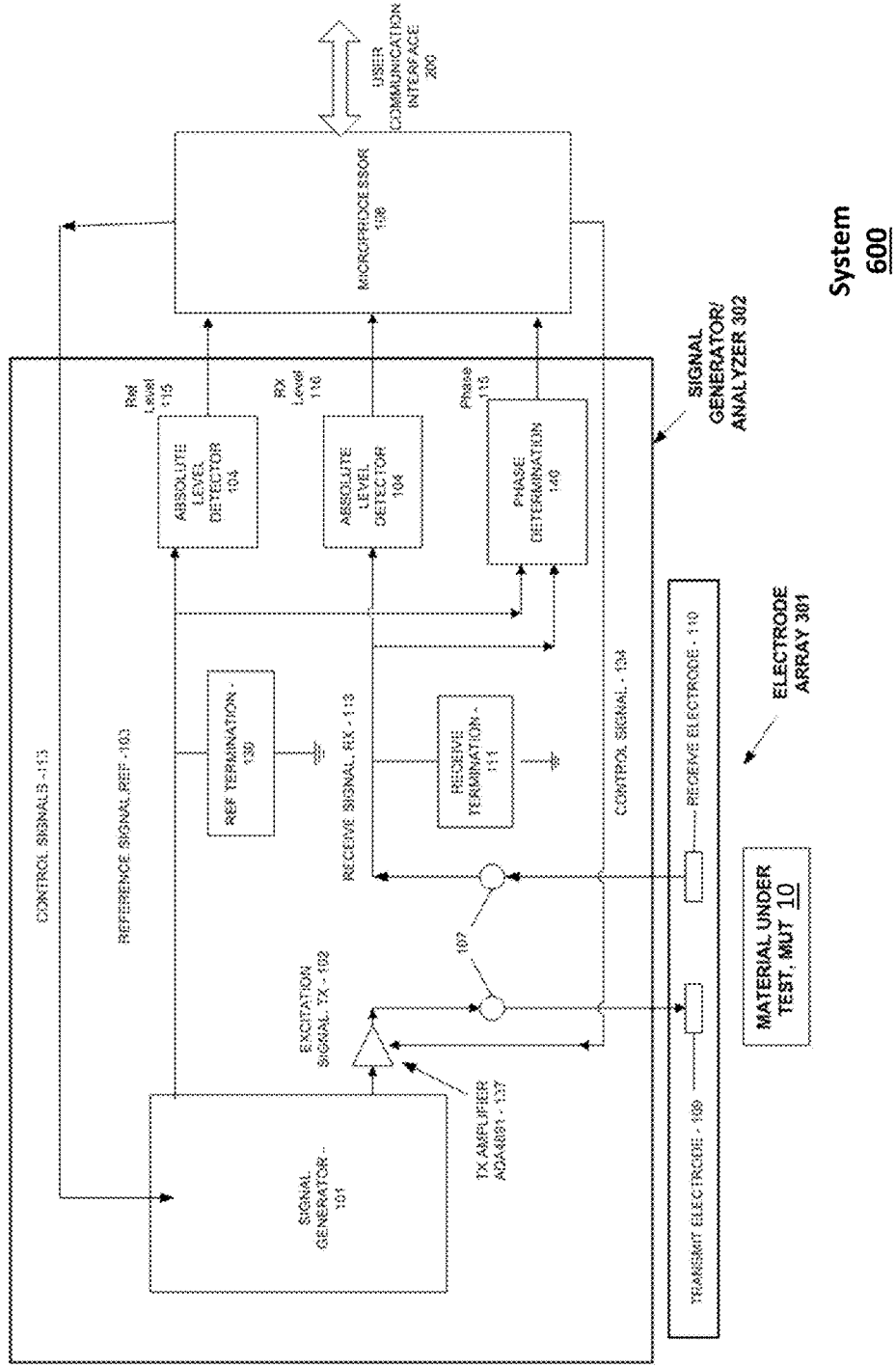
FIG. 12 shows a system according to various embodiments of the disclosure.
Figure 13:
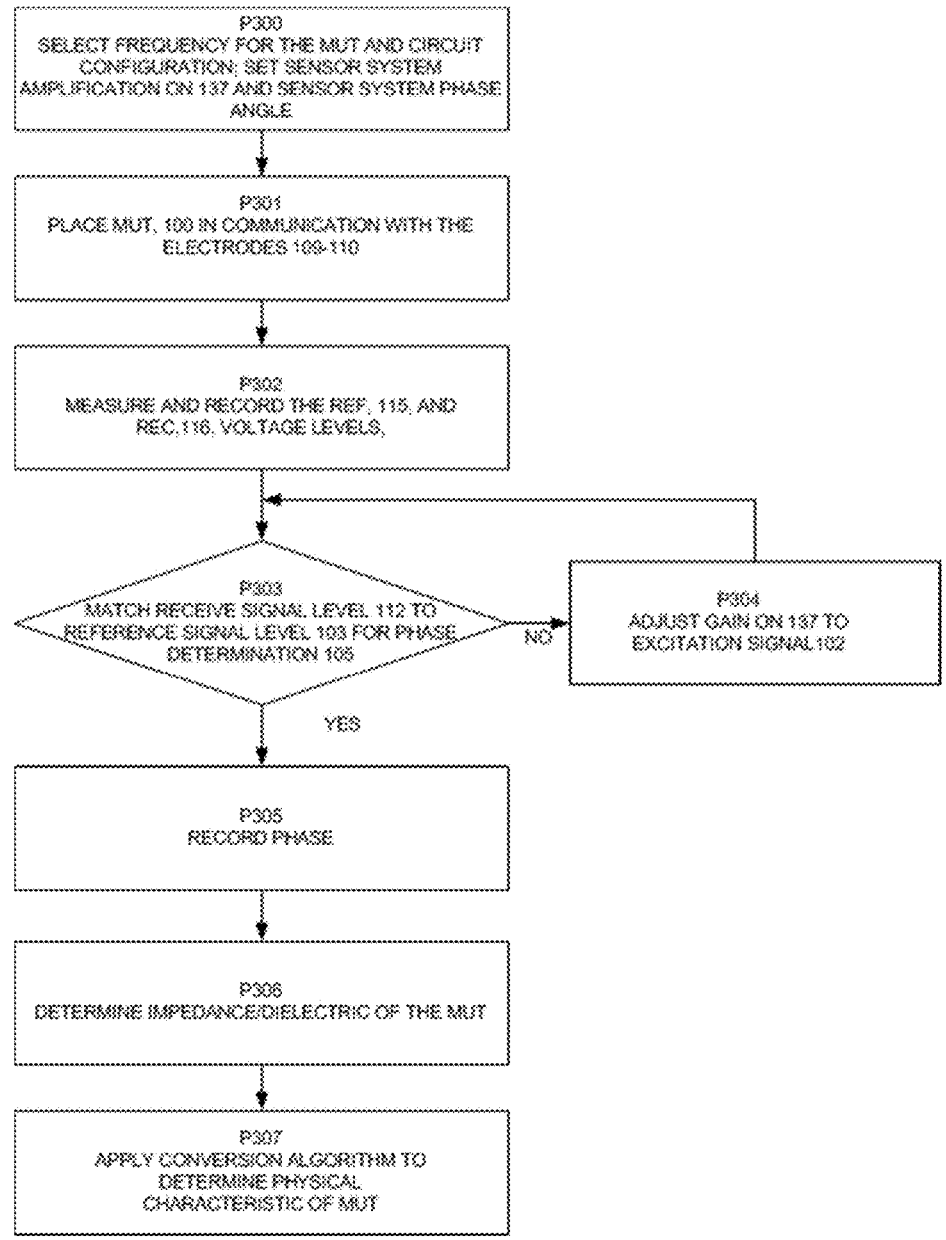
FIG. 13 shows a flow diagram illustrating a method according to various embodiments of the disclosure.

At this point, according to various embodiments, the sensor system 600 shown in FIG. 12 may be configured to measure the impedance of MUT 10. System 600 can include various components shown and described with respect to systems 100, 200, 300 and 400, discussed herein, and can include: (i) Microprocessor 106; (ii) Signal Generator/Analyzer 302 connected with microprocessor 106; (iii) electrodes 109, 110 and their related array/assembly 301, connected with signal generator/analyzer 302; and (iv) MUT 10. As shown in FIG. 13, one process for measuring the impedance of MUT 10 using system 600 can include the following sub-processes:

P300: Select the frequency specific to the MUT 10 being tested with the configuration of sensors 109, 110, and set the amplifier 137 and phase angle as determined by either process 100 or process 200;

P301: Place MUT 10, in electromagnetic communication with sensor electrodes 109, 110;

P302: Measure and record the REF level 115 and RX level 116 at microprocessor 106;

P303: Determine whether RX level 116 and REF level 115 are in the operating frequency range of the electronic components used for the phase determination (see FIG. 16).

Figure 16:
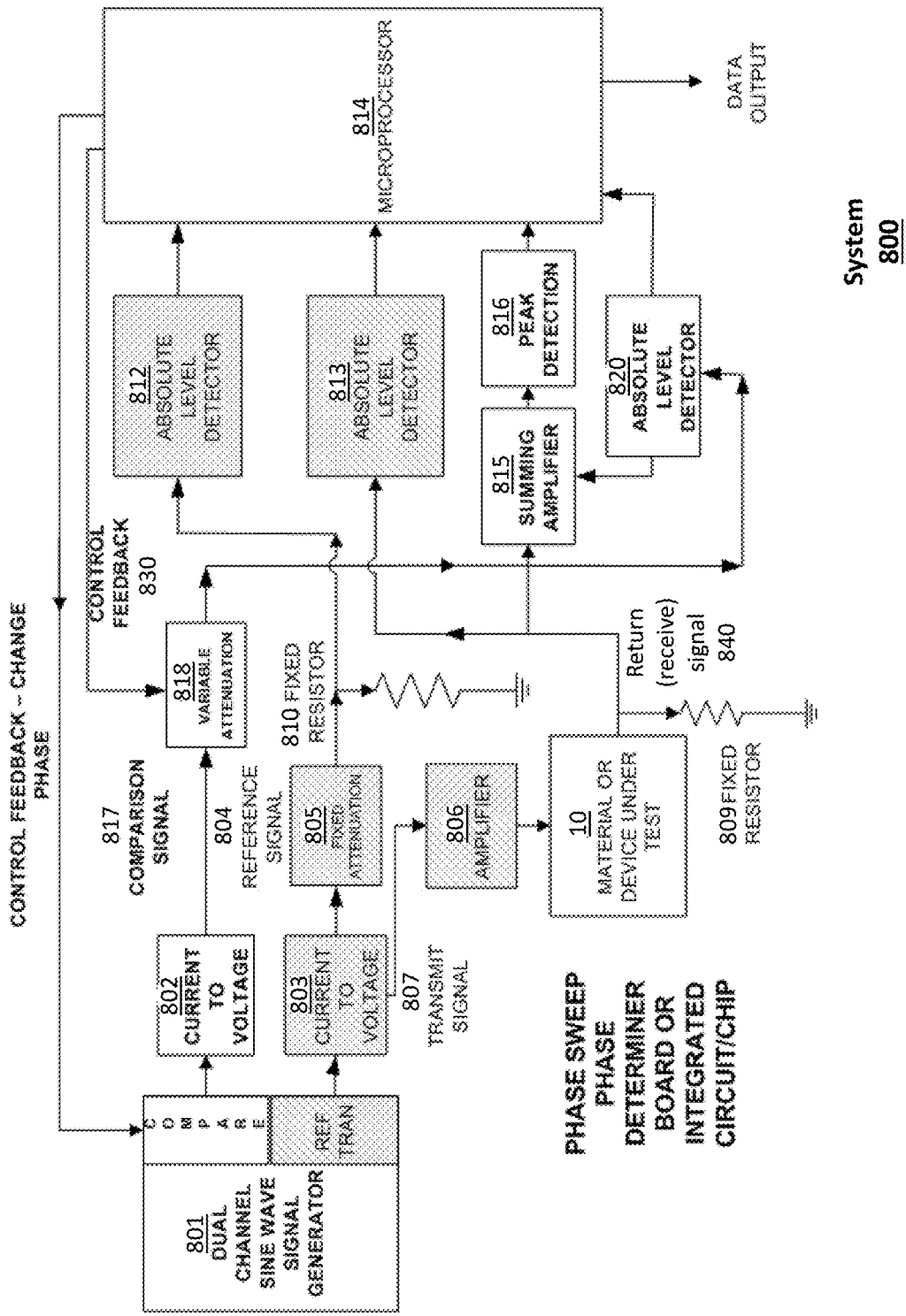
FIG. 16 illustrates a phase sweep determiner system according to various embodiments.

P304: Adjust the gain on amplifier 137 until the RX level 116 and REF level 115 are within the operating frequency range of the electronic components used for phase determination 140 (FIG. 16);

P305: Record the phase angle 117, at microprocessor 106, UCI 200 or other data storage device;

P306: Determine the impedance/dielectric of the MUT as described US Patent Publication Nos. 2013/0307564 and 2016/0161624, each of which is incorporated by reference herein; and P307: Apply the conversion algorithm to determine the desired physical characteristic of the MUT as described US Publication Nos. 2013/0307564 and 2016/0161624.

Figure 14:
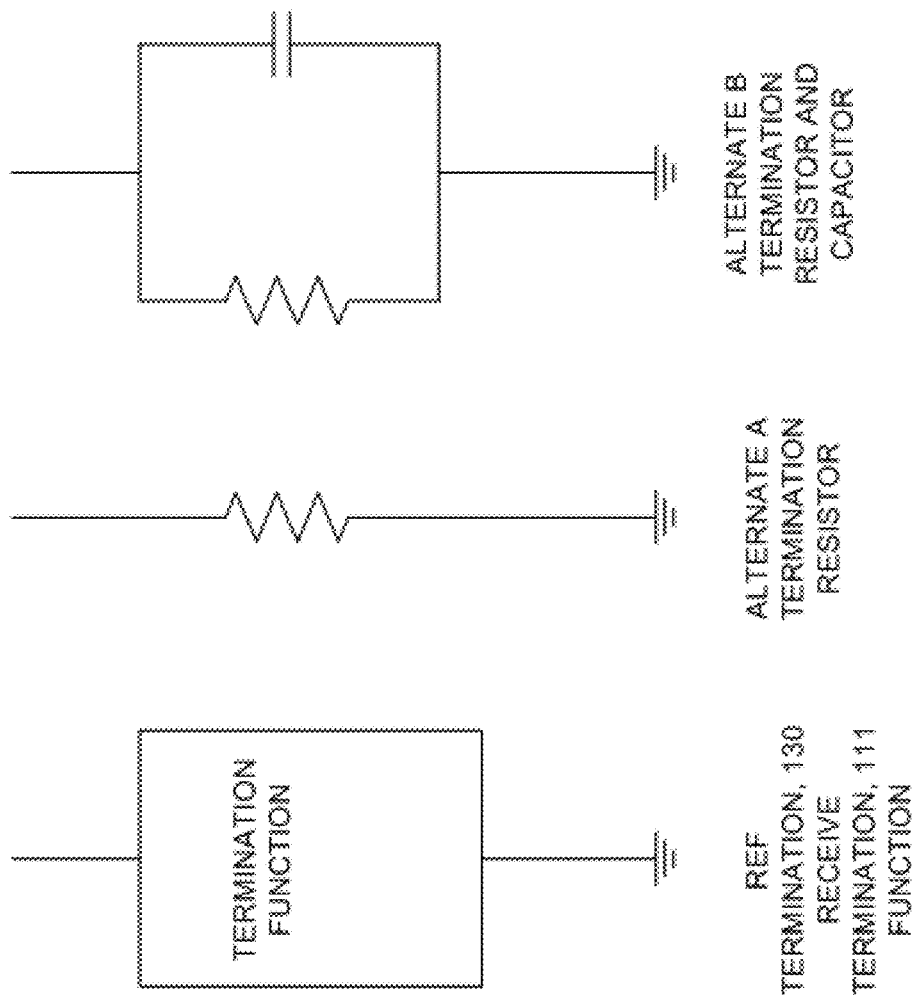
FIG. 14 illustrates alternate circuit embodiments for terminations in the system of FIG. 12, according to various embodiments of the disclosure.
Figure 15:
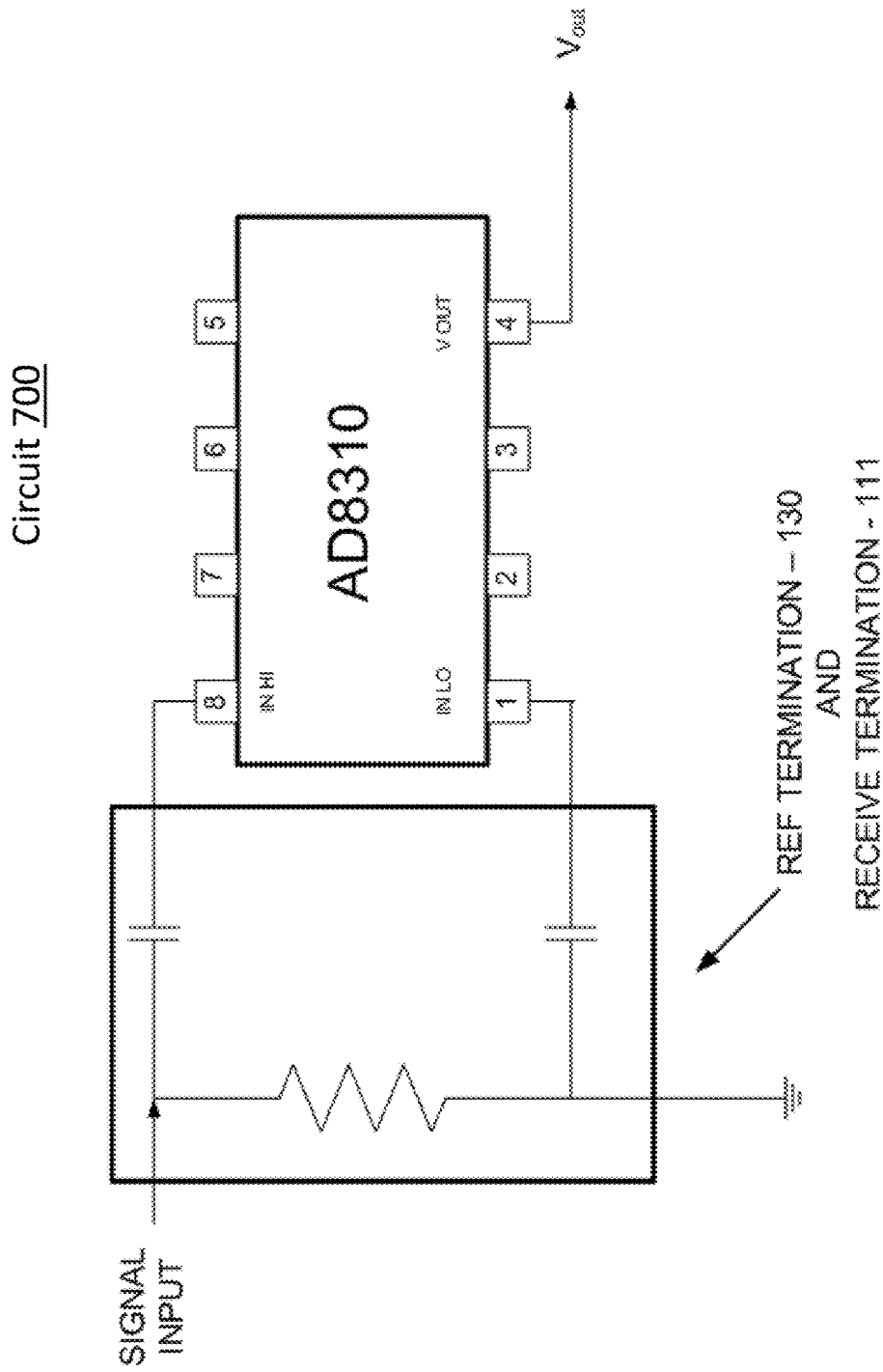
FIG. 15 illustrates a termination circuit configuration according to various embodiments of the disclosure.

Referring back to FIG. 3, and with reference to FIG. 14, the reference termination 130 and the receive termination 111, can be defined using termination functions shown in FIG. 14. Alternate A is a simple fixed resistor. Alternate B is a fixed resistor-capacitor circuit. However, according to various embodiments, the circuit 700 shown in FIG. 15 may be used as a termination circuit, incorporating both reference termination 130 and receive termination 111 functions. This termination circuit 700 can be particularly beneficial for the AD8310 version of absolute level detector 104, however, if another model of absolute level detector 104 is used, this circuit 700 or a different termination circuit may be used.

Referring again back to FIG. 3, the phase determination may be accomplished by the phase sweep method discussed herein, or the time-of-flight measurement method, also discussed herein. The shortcomings of the phase sweep method will be discussed to illustrate why the time-of-flight method using a Time-to-Digital Conversion (TDC) chip is beneficial in the systems and approaches of the present disclosure.

Referring to FIG. 16, a system 800 is shown, where system 800 is configured to perform a phase sweep method for determining the phase angle shift between two signals according to various embodiments. This embodiment uses a dual channel sine wave generator 801 to generate a set of signals, as described herein. An alternate embodiment could use two single channel sine wave generators in place of the dual channel sine wave generator 801. Dual channel sine wave generator 801 generates a signal that is divided, by a current-to-voltage converter 803, into a reference signal 804 and a transmit signal 107. Reference signal 804 is passed through a fixed attenuator 805, and then to an absolute level detector 812, as discussed with respect to various other systems herein. The output of absolute level detector 812 communicated to the microprocessor 814. Transmit signal 807 can be passed through an amplifier 806 before being transmitted through the MUT 10. The receive (return) signal 840 from MUT 10 is split, with a portion sent through a controllable amplifier (not shown, and under control of the microprocessor 814) and then to an absolute level detector 813, the output of which is communicated to a microprocessor 814. Meanwhile, reference signal 804 is transmitted through a distinct absolute level detector 812, and then to microprocessor 814. The magnitude variation between the two signals, reference 804 and receive (return), is determined and stored for use in the computation of the measure impedance of MUT 10, as described herein. The receive (return) signal 840 from MUT 10 is also transmitted to a summing amplifier 815, which is part of a phase determiner circuit. Turning back to the sine wave signal generator 801, a comparison signal 817 is generated by dual channel sine wave signal generator 801 and converted using current-to-voltage converter 802. The frequency of comparison signal 817 and (reference) transmit signal 807 are set to be identical. The relative phase angle between the two signals is varied. The size of the phase increment, e.g., one degree, can be selected by the user or designer of the system 800. In general, the range over which the phase angle between the transmit signal 807 and comparison signal 817 is shifted is ±180 degrees. In practice, however, either prior data with the system 800 and MUT 10 or an a priori analysis may provide an estimate of the expected phase angle shift between transmit signal 807 and comparison signal 817. Using this base value of the expected phase angle shift as the center of the range to be swept, a swept range of, e.g., ±20 degrees would be adequate to determine the actual phase angle of a particular measurement.

Returning to the path of comparison signal 817, after current-to-voltage conversion 802, it is passed through a variable attenuator 818, which is controlled by microprocessor 814. From the variable attenuator 818, it is transmitted to an absolute level detector 820, the output of which is communicated to microprocessor 814. After leaving absolute level detector 820, the signal is joined with the receive (return) signal 840 from MUT 10 in summing amplifier 815. The sum of the two signals is passed to a peak detector 816, the output of which is communicated to microprocessor 814.

Figure 17:
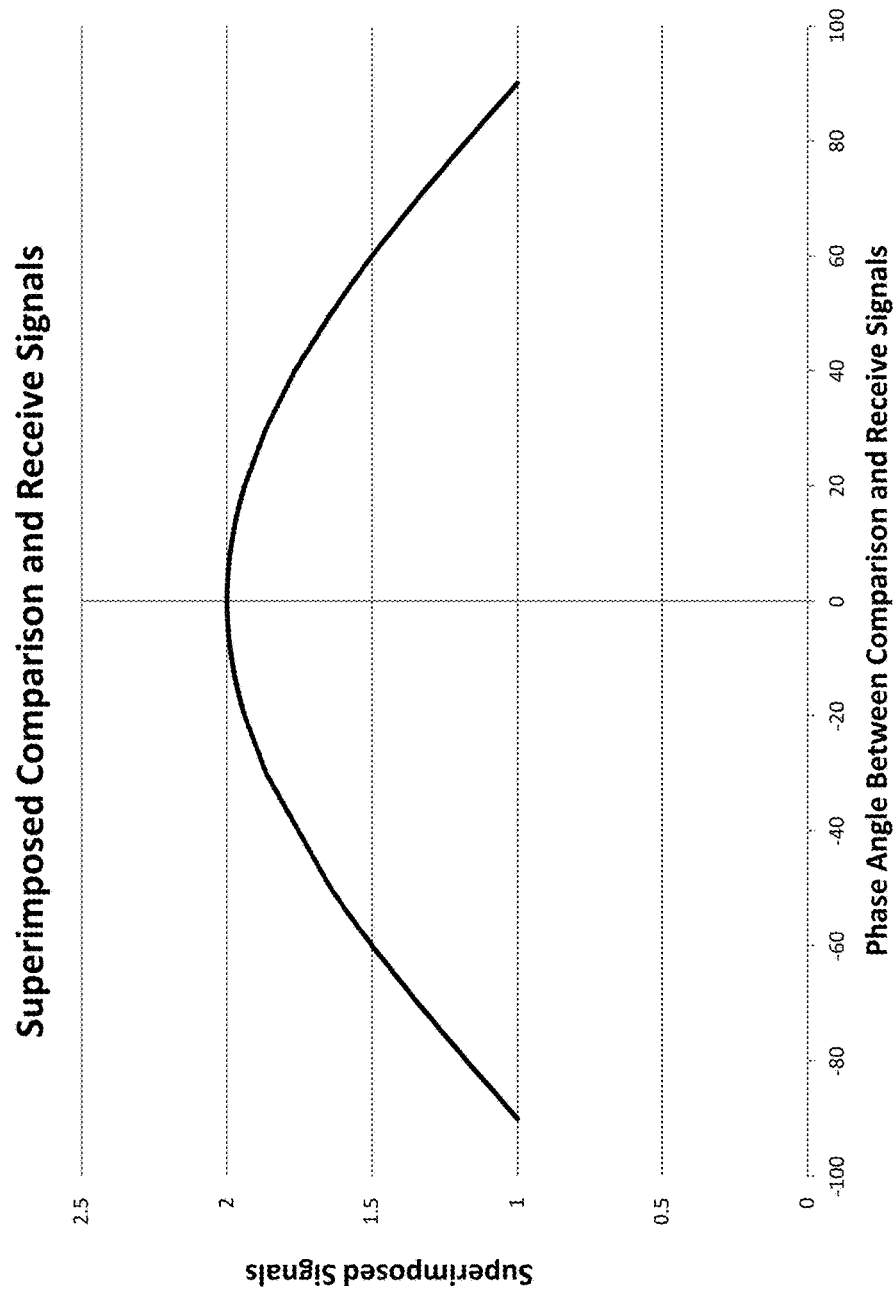
FIG. 17 is a graphical depiction of superimposed comparison signals and receive (return) signals versus phase angle shown with reference to the system of FIG. 16.

The signal from absolute level detector 820 is compared to that from the absolute level detector 813 at microprocessor 814, and used, via control feedback signal 830 to control variable attenuator 818 to modify the output signal from variable attenuator 818 to match the output signal from absolute level detector 813. When the phases of the comparison signal 817 and receive (return) signal 840 from MUT 10 are in phase, the amplification value of summing amplifier 815 will be equal to twice that of the receive (return) signal 840. When the phases of comparison signal 817 and receive (return) signal 840 from MUT 10 are ±90 out of phase, the amplification value of summing amplifier 815 is one; when ±180 out of phase, the value is zero. This is illustrated in the graphical depiction of the superimposed signals (comparison 817 and receive 840) v. phase angle of FIG. 17, where the superposition of comparison signal 817 with varying phase angles between receive signal 840 and the comparison signal 817 is made on receive signal 840.

One problem with the phase sweep approach is the amount of time required to sweep through the range of phase angles. In the most general (worse) case, there are 360 phase change readings. The time required to sweep through all 360 angles and record the data from summing amplifier 815 and peak detector 816 is about 400 milliseconds. This would not be as problematic if the measurement device is stationery, and measures the same volume of MUT 10. However, systems according to various embodiments disclosed herein are designed to allow operation on a mobile platform, e.g., as described in WO Publication No. 2016/115318 (incorporated by reference in its entirety). When a sensor system is mounted on a non-stationary component, e.g., on a pavement roller traveling several (e.g., 3) miles per hour, the sensor will move a certain distance, over time (e.g., about 1.8 feet in the 0.4 seconds), while the phase angle sweep is proceeding. In some cases, the sensor moves a plurality of feet, over fractions of a second, before the entirety of the phase angles can be swept. This does not include additional time to record and process the phase sweep data. In these scenarios, there is no guaranty that the volume of the MUT 10 being measured throughout this time (and across this distance) remains constant.

Figure 18:
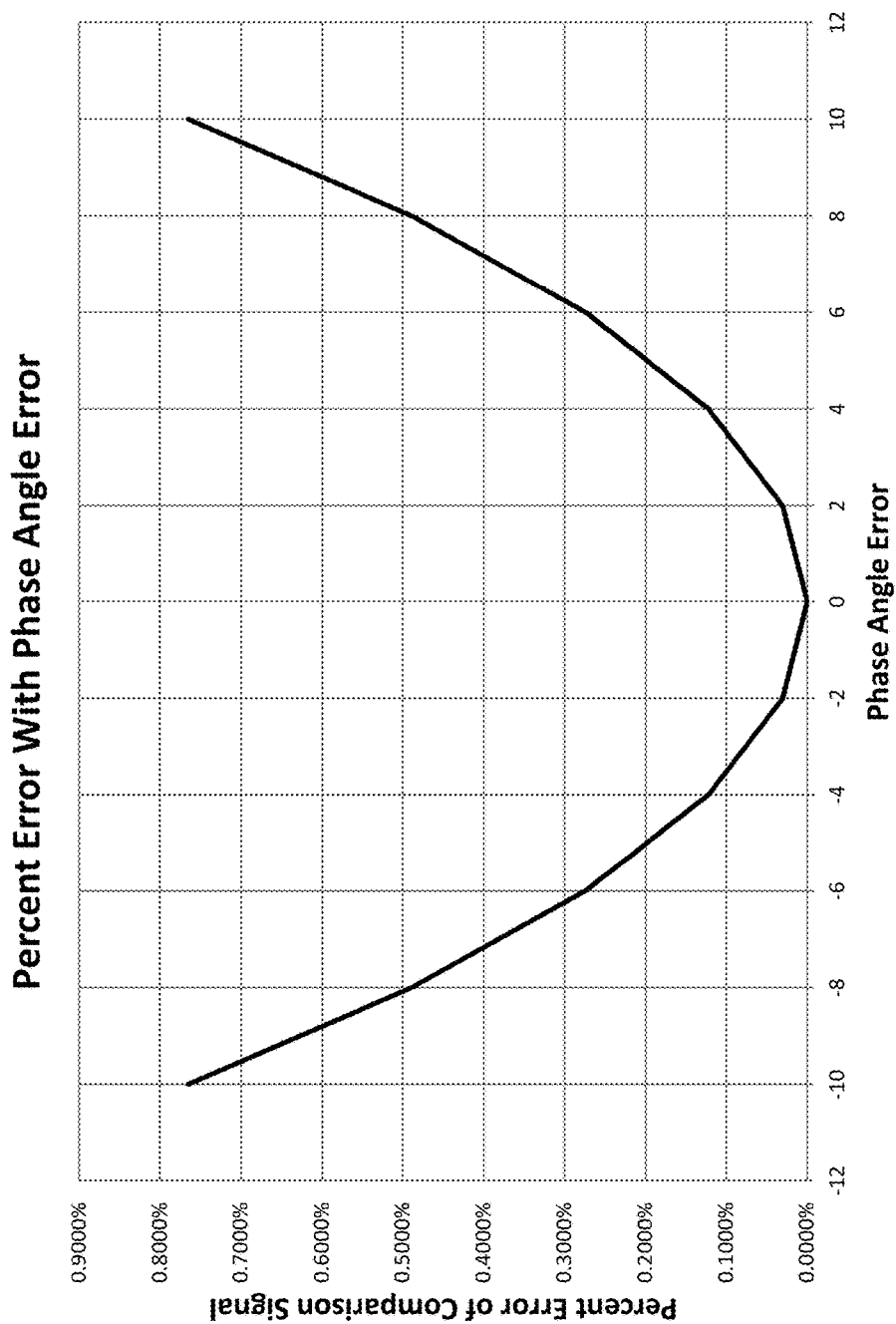
FIG. 18 is a graphical depiction of percent error versus phase angle shown with reference to the system of FIG. 16.

Another problem with the phase sweep approach relates to the precision with which the peak of the phase sweep can be identified. The characteristic of summing two sine waves is that at the peak, the signal becomes flat. This is illustrated in the graphical depiction of the phase sweep in FIG. 17 based upon system 800. This graphical characteristic illustrates the principle that as the peak is approached, the amount of signal change with the phase angle becomes smaller. This is illustrated in FIG. 18, which shows a graphical depiction of percent error for comparison signal 817 versus phase angle error. As shown, an error of less ±0.8% in the reading of the summed signal can result in an error in the determination of the correct phase angle between the two signals of up to ±10 degrees.

These and other problems with the phase sweep phase approach make it embodiment particularly challenging approach to implement in a moving system.

Figure 19:
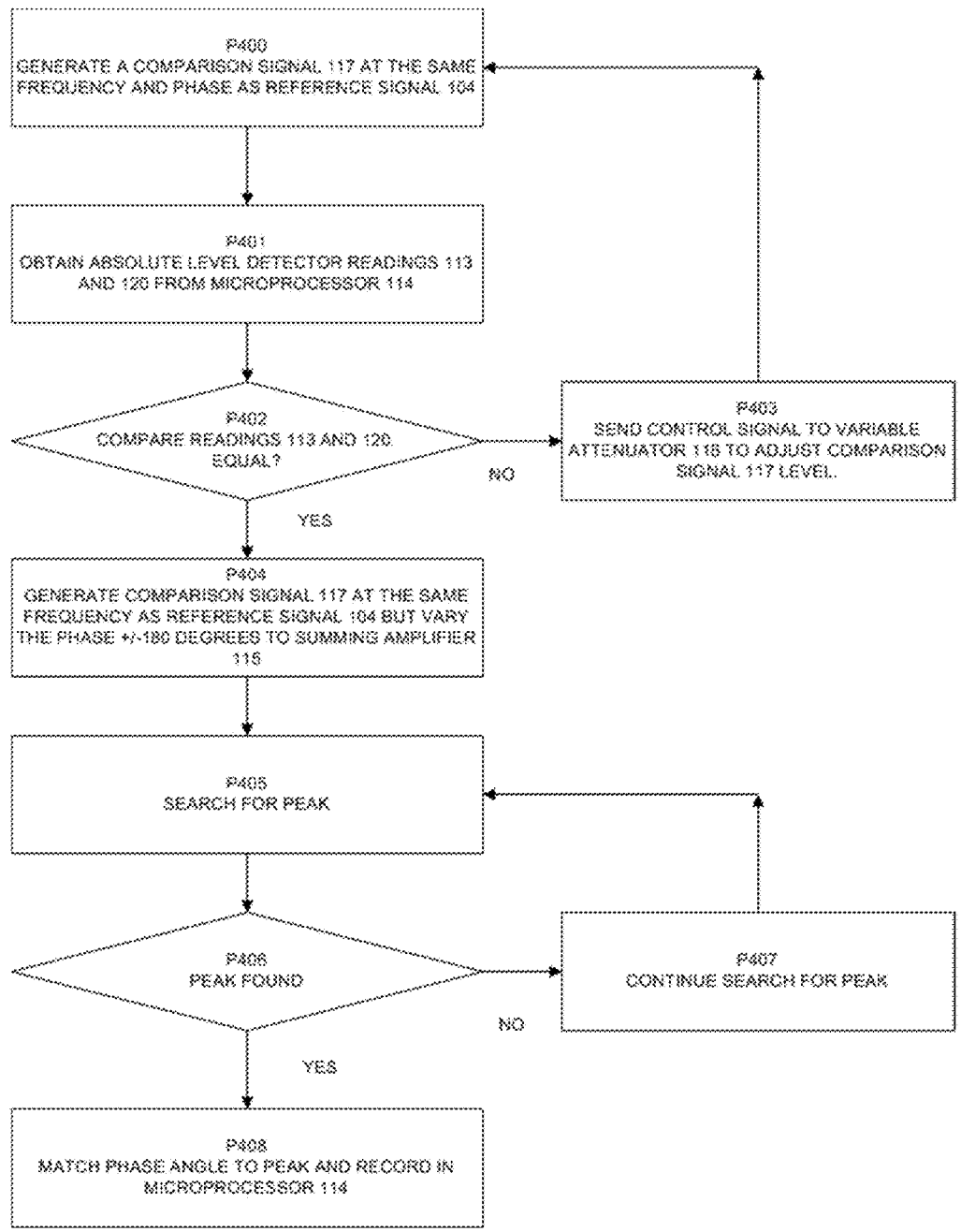
FIG. 19 shows a flow diagram illustrating a method of performing phase determination according to embodiments of the disclosure.

FIG. 19 shows a flow diagram for system 800 (FIG. 16) illustrating a method for determining a phase angle difference between receive signal 840 and comparison signal 817 according to various embodiments of the disclosure. This flow diagram is discussed with continuing reference to FIGS. 1, 3, 4, 9, 12, 16, 20, and 21, but may be particularly applicable to system 800 in FIG. 16. As shown, the process can include:

Process P400: Generate a comparison signal 817 in signal generator 801 with the same frequency as reference signal 804 and transmit signal 807, and at the same phase angle.

Process P401: Obtain the readings for the receive Signal 840 from absolute level detector 813 and for the comparison signal from absolute level detector 820 from microprocessor 814.

Process P402: Compare the values of readings from absolute level detector 813 and absolute level detector 820 to determine if they are equal. If yes, proceed to P404; if not, proceed to P403.

Process P403: Send a control feedback signal 830 to variable attenuator 818 to adjust the level of comparison signal 817 so that the readings of absolute level detector 813 and absolute level detector 820 are equal.

Process P404: Generate a series of comparison signals 817 in signal generator 801 with the same frequency as reference signal 804 and transmit signal 807, but varying the phase angle ±180 degrees. The resulting comparison signal 817 from the phase sweep process are directed along with receive signal 840 to the summing amplifier 815.

Process P405: Searching for the peak in the phase sweep, which may be accomplished in a number of different ways. As shown in FIG. 16, a peak detection circuit 816 may be used to detect the peak in the phase sweep. Alternately, a computational method may be used in which a series of moving averages may be computed and compared. However, as shown in FIG. 18 and discussed herein, the variation in signal strength as the phase angle is matched is very small. As such, small errors in the determination of the superimposed signal strength can result in large errors of the selected phase angle.

Process P406: Conduct a test to determine if the peak value of summing amplifier 815 has been determined. If yes, proceed to P408; if no, proceed to P407.

Process P407: Continue to search for the peak across the phase sweep if the result of P406 is negative.

Process P408: Record the identified value of the phase angle difference between comparison signal 817 and receive signal 840 in the microprocessor 814 for the computation of the impedance or dielectric of MUT 10.

Figure 20:
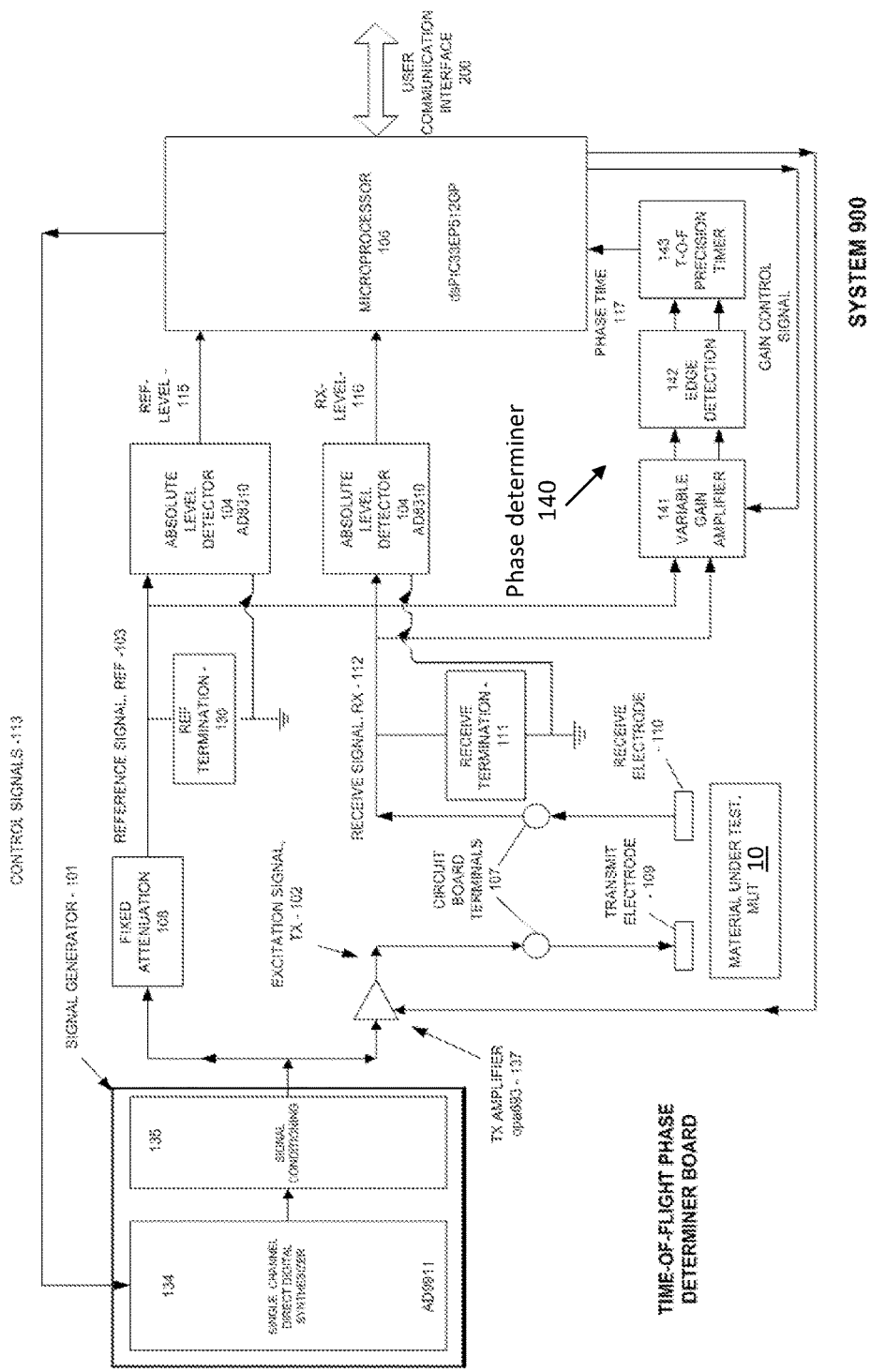
FIG. 20 illustrates a time-of-flight phase determination system according to various embodiments of the disclosure.

Turning now to FIG. 20, a system 900 for computing phase using a time-of-flight approach according to various embodiments is shown. System 900 may have some similar components as system 200 shown in FIG. 3. System 900 can additionally include a phase determiner 140, including time-of-flight circuit components such as a variable gain amplifier 141, an edge detector 142, and a time-of-flight precision timer 143. According to various embodiments of the disclosure phase determiner 140 enhances the phase shift calculation compared with conventional systems, and allows system 900 to precisely calculate phase shift between signals, as described herein.

Figure 21:
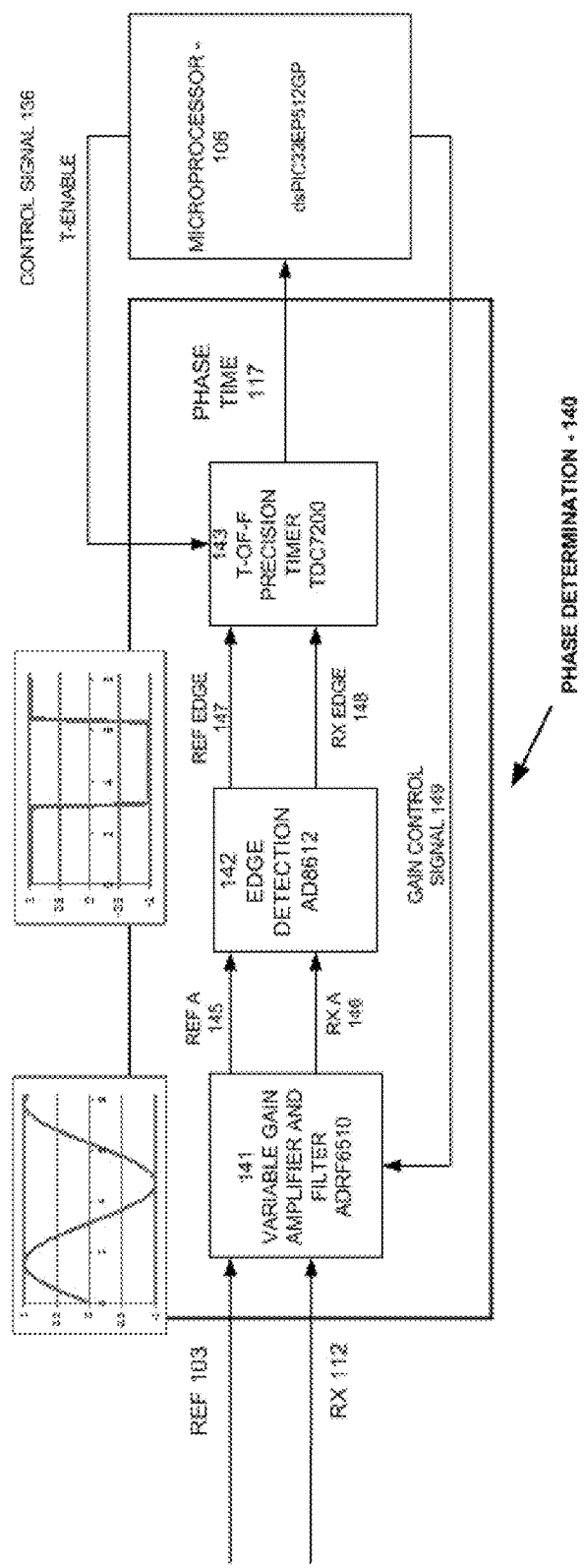
FIG. 21 illustrates an embodiment of methodology phase determination system according to various embodiments of the disclosure.

An example of phase determiner 140 using the time-of-flight approach is shown according to various embodiments in FIG. 21. The time-of-flight circuit (system 900) includes phase determiner 140, which may include a precision timer 143. Precision timer 143 may provide a digital reading of the time between two triggers. In some cases, phase determiner 140 is designed to provide a response similar to a Time-to-Digital Conversion chip (e.g., Texas Instruments TDC7200), however, other conventional models could be used as well. In order to provide a proper trigger signal, the sinusoidal reference signal 103 and receive signal 112 are converted into a square wave. This can be accomplished, for example, by using an edge detector 142 (e.g., the Analog Devices AD8612 chip or another conventional model). However, in the example of AD8612 as edge detector 142, this chip has a limited input dynamic range. In this example, in order to assure that the incoming signals are within the dynamic range of the AD8612 chip, the signals are passed through a dual channel variable gain amplifier 141, which may include an ADRF6510 amplifier in some example embodiments. As shown in FIG. 21, the edge detector 142 chip can convert the sinusoidal ref signal 103 and receive signal 112 to square waves, which can be transmitted to the precision timer 143, which provides a digital reading of the time between the zero crossings of the two signals. This digital time is then transmitted to the microprocessor 106. Because the quality of the signal passing through the edge detector 142 is dependent on the incoming signals being within the dynamic voltage range of the chip, the timing detected by the precision timer 143 may be unstable. In these cases, microprocessor 106 can evaluate the phase time signal 117 from the precision timer 143 to determine whether that phase time signal 117 is stable, and if not, microprocessor 106 instructs variable gain amplifier 141 (via gain control signal 149) to modify one of its gain settings. Microprocessor 106 iterates this process until phase time signal 117 received from precision timer 143 is stable. The computation of the phase angle between reference signal 103 and receive signal 112 is based on the time measured by the phase determiner 140, as described above, and the cycle time of the signals. The cycle time (or, period) of a signal is equal to the inverse of its frequency. For example, the frequency of the excitation signal 102 used to determine the density of hot mix asphalt is 13.6 MHz. In one example, the DDS 134 (e.g., AD9911 chip) has a frequency accuracy of at least 0.1 Hz. Thus, in the example of hot mix asphalt, the time for one cycle of the signal is $73.52 \times 10^{-9}$ seconds (or 73.52 nanoseconds). In another example, the precision timer 143 (e.g., TDC7200 chip) has a specification sheet standard deviation of $35 \times 10^{-12}$ seconds, and a resolution of $55 \times 10^{-12}$ seconds (or 55 picoseconds). As the resolution in this precision timer 143 is larger than the standard deviation, computation of the phase angle requires additional calculation. More specifically, because the chip measures two times (at the time from trigger for each wave), the potential resolution error of the phase time is $78 \times 10^{-12}$ seconds, which is equal to the square root of the sum of the squares of the resolution (standard deviation). In these cases, in order to compute the phase angle, the following equation may be used:

$$\text{Phase Angle} = 360 \times (\text{Phase Time}/\text{Cycle Time})$$

The potential error with this method (e.g., one standard deviation/resolution) at an example frequency of 13.6 MHz is 0.337 degrees.

The above-noted approaches may have an inherently better precision than conventional approaches, e.g., the phase sweep approach described in US Patent Publication 2014/0266268 (also incorporated by reference herein in its entirety), and may also reduce cycle time for measuring phase angles relative to those conventional methods. In some cases, the inventors sampled with a cycle time of 73.52 picoseconds, and a requirement of acquiring time data from five cycles, and determined the phase in less than 0.5 microseconds (including processing time). This short cycle time can be particularly beneficial when measurements are being made, e.g., from a moving vehicle, such as in circumstances indicated in Provisional U.S. Patent Application No. 62/103,835.

Figure 22:
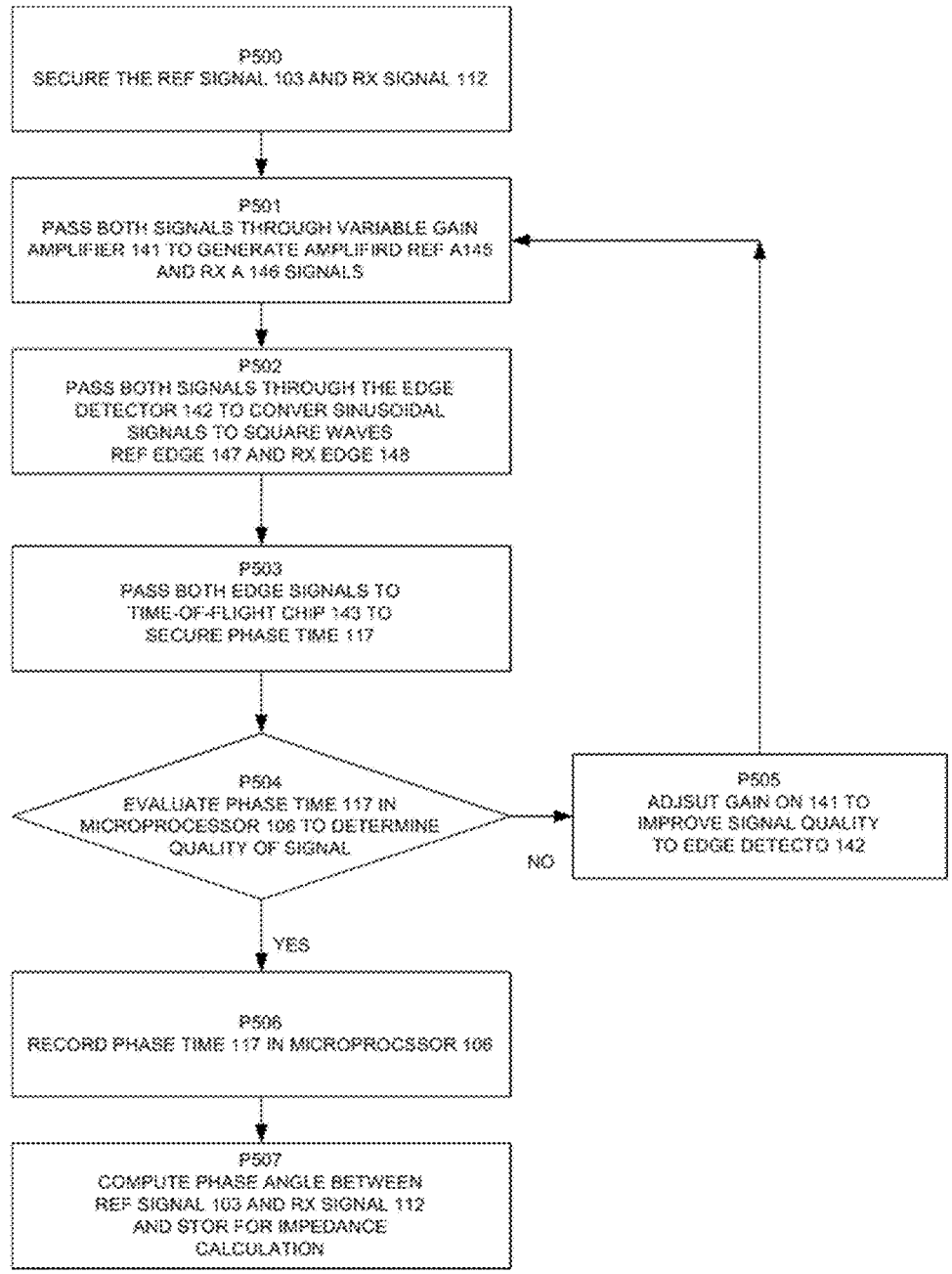
FIG. 22 shows a flow diagram illustrating a method for determining a phase angle according to various embodiments of the disclosure.

FIG. 22 shows a flow diagram illustrating a method for determining a phase angle according to various embodiments of the disclosure based on the time-of-flight approach. This flow diagram is discussed with continuing reference to FIGS. 1, 3, 4, 9, 12, 16, 20, and 21. As shown, the process can include:

Process P500: obtaining reference signal 103 and RX signal 112.

Process P501: passing both reference signal 103 and RX signal 112 through variable gain amplifier 141 (FIG. 21) to generate an amplified reference A signal 145 and RX A signal 146.

Process P502: pass both reference signal 103 and RX signal 112 through edge detector 142 (FIG. 21) to convert these sinusoidal signals to square waves, ref. edge signal 147 and RX edge signal 148.

Process P503: pass both ref. edge signal 147 and RX edge signal 148 to time-of-flight calculator 143 to determine a phase time 117.

Process P504: evaluate phase time 117 at computing device (e.g., microprocessor 106) to determine quality of signal.

Process P505: if signal quality is poor (below threshold quality level), adjust gain on amplifier 141 to improve quality to edge detector 142.

Process P506: if signal quality is good (above threshold quality level), record phase time 117 in computing device.

Process P507: compute phase angle between ref signal 103 and RX signal 112 and store at computing device for impedance calculation.

Figure 23:
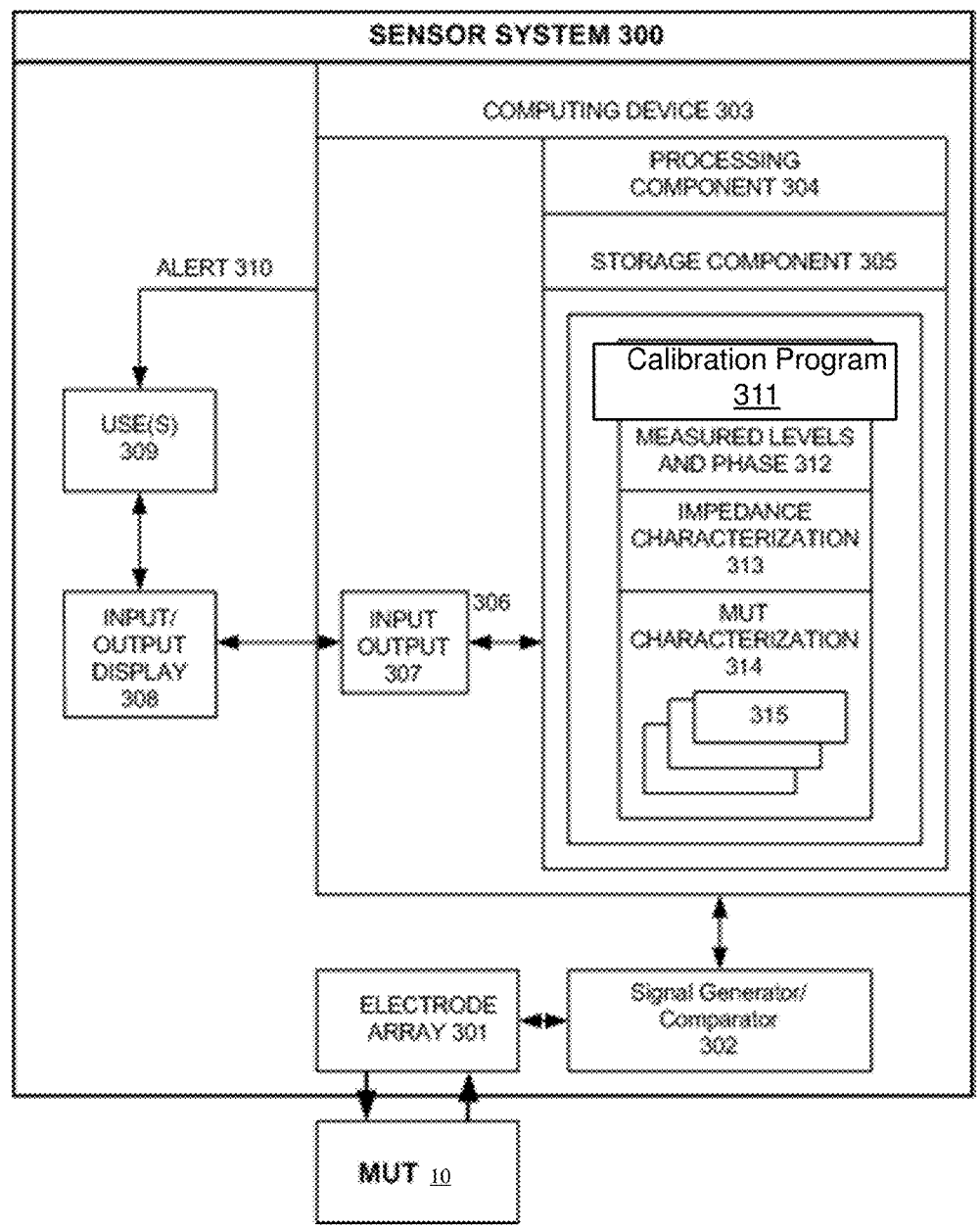
FIG. 23 shows a sensor system according to various embodiments of the disclosure.

FIG. 23 depicts an illustrative environment including a sensor system 300 configured to secure complex impedance readings of an MUT 10, and correlate the readings to a physical parameter of the MUT 10 according to various embodiments. To this extent, sensor system 200 includes a computing device 303 that can perform processes described herein in order to control measurement parameters and detect an impedance response of MUT 10. In particular computing device 303 is shown as including a processing component 304, and a storage component 305, which makes sensor system 300 operable to detect an impedance response of MUT 10 and characterizing a physical parameter by performing any/all of the processes described herein and implementing any/all of the embodiments described herein.

Computing device 303 is shown including a processing component 304 (e.g., one or more processors), a storage component 305 (e.g., a storage hierarchy), an input/output pathway 306, and an input/output (I/O) component 307, which can connect to one or more I/O interfaces and/or devices such as input/output display 308. In general, processing component 304 executes program code, which is at least partially fixed in storage component 305.

While executing program code, processing component 304 can process data, which can result in reading and/or writing transformed data from/to the storage component 305 and/or the I/O component 307, for further processing. The I/O Component 307 and/or I/O display 308, can comprise one or more human I/O devices, which enable a human user(s) 309 to interact with the computing device 303, and/or one or more communications devices to enable a system user(s) to communicate with computing device 303 using any type of communications link. To this extent, a Calibration Program 311, the Measurement Program, 312, the Impedance Program, 313, and the MUT Characterization Program, 315, can manage a set of interfaces (e.g., graphical user interface(s), application program interface, etc.) that enable human and/or system users to interact with the Computing Device and the Sensor System.

In any event, the Computing Device, 303, can comprise one or more general purpose computing articles of manufacture (e.g., computing devices) capable of executing any of the stored program codes, 311, 312, 313, and 314, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression.

Further, the any of the stored programs can be implemented using a set of modules, 315. In this case, a module, 315, can enable the Computing Device, 303, to perform a set of tasks used by any of the stored programs, and can be separately developed and/or implemented apart from other portions of impedance programs. As used herein, the term "component" means any configuration of hardware, with or without software, which implements the functionality described in conjunction therewith using any solution, while the term "module" means program code that enables the computer system Computing Device to implement the functionality described in conjunction therewith using any solution. When fixed in a Storage Component, 305, of a Computing Device, 303, that includes a Processing Component, 304, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the Sensor System, 300.

When the Sensor System 300 comprises multiple computing devices, each computing device may have only a portion of the stored programs fixed thereon (e.g., one or more modules 315). However, it is understood that the Sensor System, 300, and stored processing programs are only representative of various possible equivalent computer systems that may perform a process described herein. To this extent, in other embodiments, the functionality provided by the Sensor System 300 and any of the stored processing programs, 311 through 315, can be at least partially implemented by one or more computing devices that include any combination of general and/or specific purpose hardware with or without program code. In each embodiment, the hardware and program code, if included, can be created using standard engineering and programming techniques, respectively.

Regardless, when the Sensor System 300 includes multiple computing devices, the computing devices can communicate over any type of communications link. Further, while performing a process described herein, the Computing Device, 303, of the Sensor System 300 can communicate with one or more other computing devices using any type of communications link. In either case, the communications link can comprise any combination of various types of wired and/or wireless links; comprise any combination of one or more types of networks; and/or utilize any combination of various types of transmission techniques and protocols.

The Sensor System 300 can obtain or provide data, such as Calibration Data 311 or Measured Levels and Phase Data 312, for solution processing, e.g., by program(s) 312, 314, or 315.

While shown and described herein as a method and system for impedance detection and computation, it is understood that aspects of the invention further provide various alternative embodiments. For example, in one embodiment, the invention provides a computer program fixed in at least one computer-readable medium, which when executed, enables a computer system to control impedance detection and correlation parameters. To this extent, the computer readable medium includes program code, such as the impedance measurement program 312 (FIG. 20), which implements some or all of the processes and/or embodiments described herein. It is understood that the term "computer readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

We claim:

1. A system comprising:
   a signal generator;
   a transmitting electrode connected with the signal generator and in electromagnetic communication with a material under test (MUT);
   a receiving electrode connected with the signal generator and in electromagnetic communication with the material under test (MUT);
   a reference level detector connected with the signal generator in parallel with the transmitting electrode;
   an absolute level detector connected with the receiving electrode;
   a phase determiner connected with the receiving electrode and the signal generator; and
   at least one computing device connected with the signal generator, the phase determiner, the reference level detector, and the absolute level detector, the at least one computing device configured to:
      send a control signal to the signal generator to initiate: an excitation signal to the MUT via the transmitting electrode at a selected frequency, and a reference signal to the reference level detector;
      receive a reference level signal from the reference level detector;
      receive a return signal from the MUT via the receiving electrode and the absolute level detector;
      receive a phase signal from the phase determiner; and
      record the reference level signal, the phase signal and the return signal.

2. The system of claim 1, wherein the at least one computing device is further configured to compare an impedance of the return signal with an impedance of the excitation signal to determine a characteristic of the MUT, and wherein the characteristic includes at least one of density, water content, or physical composition.

3. The system of claim 1, further comprising:
   a set of circuit board terminals connected with the signal generator, the transmitting electrode, the receiving electrode, and the absolute level detector; and
   a calibration circuit coupled with the circuit board terminals, the calibration circuit configured to short circuit the circuit board terminals, wherein the at least one computing device is further configured to:
      receive a calibration signal from the circuit board terminals; and
      modify the control signal to the signal generator in response to the calibration signal deviating from the reference level signal by greater than a threshold.

4. The system of claim 3, wherein the threshold is equal to approximately a one percent deviation.

5. The system of claim 3, wherein the modifying of the control signal to the signal generator includes providing instructions to adjust the excitation signal to the transmitting electrode by an amount corresponding with the deviation between the calibration signal and the reference signal.

6. The system of claim 1, further comprising an amplifier connected with and located between the signal generator and the transmitting electrode, the amplifier for amplifying the excitation signal prior to transmission into the MUT.

7. The system of claim 6, further comprising a fixed level attenuator connected with and located between the signal generator and the reference level detector, wherein the fixed level attenuator is configured to decrease an amplitude of the reference signal to approach an amplitude of the receive signal.

8. The system of claim 7, further comprising:
   a set of circuit board terminals connected with the signal generator, the transmitting electrode, the receiving electrode, and the absolute level detector; and
   a calibration circuit coupled with the circuit board terminals, the calibration circuit configured to apply at least one of a resistive or a capacitive load across the set of circuit board terminals, wherein the at least one computing device is further configured to:
      receive a calibration signal from the circuit board terminals; and
      modify the control signal to the signal generator in response to the calibration signal deviating from the reference level signal by greater than a threshold.

9. The system of claim 8, wherein the applying of the at least one of the resistive or the capacitive load includes applying both the resistive load and the capacitive load across the set of circuit board terminals, wherein the resistive load and the capacitive load are selected based upon an emulated impedance of the MUT.

10. The system of claim 8, wherein the at least one computing device is further configured to:
   iteratively send a control signal to the amplifier to adjust a gain on the amplifier until the calibration signal deviates from the reference level signal by less than or equal to the threshold.

11. The system of claim 10, wherein the at least one computing device is further configured to:
   store an amplification value corresponding with the calibration signal deviating from the reference signal by less than or equal to the threshold.

12. The system of claim 11, wherein the at least one computing device is further configured to:

store a corresponding phase angle for the reference signal and the receive signal at the amplification value, received from the phase determiner.

13. The system of claim 7, further comprising a time-of-flight phase determiner coupled with the fixed level attenuator and the receiving electrode, the time-of-flight phase determiner including:
a variable gain amplifier;
an edge detector coupled with the variable gain amplifier; and
a time-of-flight precision timer coupled with the edge detector and the at least one computing device.

14. The system of claim 13, wherein the edge detector is configured to convert sinusoidal aspects of the reference signal and the return signal to respective square waves, wherein the time-of-flight precision timer is configured to measure a time between edges of the respective square waves, and wherein the at least one computing device is further configured to compute a phase angle between the reference Signal and the return signal according to the following:

phase angle=360×(phase time/cycle time).

15. The system of claim 6, further comprising:
an MUT calibration circuit coupled with the transmit electrode and the receive electrode, the MUT calibration circuit configured to emulate an impedance response of the MUT at the receive electrode, wherein the at least one computing device is further configured to:
receive a calibration signal from the transmit electrode; and
modify the control signal to the signal generator in response to the calibration signal deviating from the reference level signal by greater than a threshold.

16. The system of claim 15, wherein the calibration circuit includes an equivalent electrode array configured to emulate the impedance response of the MUT.

17. The system of claim 16, wherein the at least one computing device is further configured to:
iteratively send a control signal to the amplifier to adjust a gain on the amplifier until the calibration signal deviates from the reference level signal by less than or equal to the threshold;
store an amplification value corresponding with the calibration signal deviating from the reference signal by less than or equal to the threshold;
store a corresponding phase angle for the reference signal and the return signal at the amplification value, received from the phase determiner;
iteratively send a control signal to the amplifier to adjust a gain on the amplifier until the return signal and the reference level signal are within an operating range of the phase determiner; and
store a phase angle of the control signal corresponding with the return signal and the reference level signal being within the operating range of the phase determiner.

18. The system of claim 1, wherein the signal generator includes a direct digital synthesizer and a signal conditioner.

19. The system of claim 1, wherein the absolute level detector provides an analog value of an absolute magnitude of a voltage of the reference signal to the at least one computing device.

20. A system comprising:
an electromagnetic signal generator operating at a fixed frequency or over a range of frequencies generating two parallel signals, a Reference Signal and a Transmit Signal;
a transmitting electrode connected with the Transmit Signal from the signal generator and in electromagnetic communication with a material under test (MUT);
a receiving electrode connected in electromagnetic communication with the material under test (MUT) generates a Receive Signal;
a reference absolute level detector connected with the Reference Signal from the signal generator;
a receive absolute level detector connected with the Receive Signal from the receiving electrode;
a time-of-flight phase determiner means connected with the Receive Signal from the receiving electrode and the Reference Signal from the signal generator; and
at least one computing device connected with the signal generator, the phase determiner, the reference absolute level detector, and the receive absolute level detector, the at least one computing device configured to:
send a control signal to the signal generator to initiate: an excitation signal to the MUT via the transmitting electrode at a selected frequency or over a range of frequencies, and a reference signal to the reference absolute level detector;
receive a reference level signal from the reference absolute level detector;
receive a return Receive Signal from the MUT via the receiving electrode and the absolute level detector;
receive a phase signal from the phase determiner; and
record the Reference Signal level, the phase signal, and the Receive Signal level.

* * * * *